US012071452B2

(12) United States Patent
Purkayastha et al.

(10) Patent No.: US 12,071,452 B2
(45) Date of Patent: Aug. 27, 2024

(54) STEVIA-DERIVED MOLECULES, METHODS OF OBTAINING SUCH MOLECULES, AND USES OF THE SAME

(71) Applicants: PURECIRCLE USA INC., Westchester, IL (US); THE COCA-COLA COMPANY, Atlanta, GA (US)

(72) Inventors: Siddhartha Purkayastha, Chicago, IL (US); Avetik Markosyan, Yerevan (AM); Siew Yin Chow, Selangor (MY); Indra Prakash, Alpharetta, GA (US); John Clos, Newnan, GA (US); Ivory Xingyu Peng, Marietta, GA (US); Michael Z. Kagan, Atlanta, GA (US); Steven F. Sukits, Fayetteville, GA (US); Kasi V. Somayajula, Marietta, GA (US)

(73) Assignees: PURECIRCLE USA INC., Westchester, IL (US); THE COCA-COLA COMPANY, Atlanta, GA (US)

( * ) Notice: Subject to any disclaimer, the term of this patent is extended or adjusted under 35 U.S.C. 154(b) by 1382 days.

(21) Appl. No.: 16/349,946

(22) PCT Filed: Nov. 14, 2017

(86) PCT No.: PCT/US2017/061581
§ 371 (c)(1),
(2) Date: May 14, 2019

(87) PCT Pub. No.: WO2018/090020
PCT Pub. Date: May 17, 2018

(65) Prior Publication Data
US 2023/0132596 A1    May 4, 2023

Related U.S. Application Data

(60) Provisional application No. 62/421,700, filed on Nov. 14, 2016.

(51) Int. Cl.
*C07H 15/256* (2006.01)
*A23L 2/60* (2006.01)
*A23L 27/30* (2016.01)
*A23L 29/30* (2016.01)
*A61K 47/26* (2006.01)

(52) U.S. Cl.
CPC ............. *C07H 15/256* (2013.01); *A23L 2/60* (2013.01); *A23L 27/36* (2016.08); *A23L 29/30* (2016.08); *A61K 47/26* (2013.01)

(58) Field of Classification Search
None
See application file for complete search history.

(56) References Cited

U.S. PATENT DOCUMENTS

| 8,916,138 B2 | 12/2014 | Abelyan et al. |
| 2013/0064955 A1 | 3/2013 | Miguel et al. |
| 2014/0342043 A1* | 11/2014 | Bell ................. A23L 2/60 426/72 |
| 2016/0039856 A1 | 2/2016 | Prakash et al. |
| 2016/0198748 A1 | 7/2016 | Prakash et al. |

FOREIGN PATENT DOCUMENTS

| JP | H01-319494 | 12/1989 |
| JP | 2015-519059 | 7/2015 |
| WO | 2013/036767 | 3/2013 |
| WO | 2013/176738 | 11/2013 |
| WO | 2014107642 A1 | 7/2014 |
| WO | 2014146135 A2 | 9/2014 |
| WO | 2016/086108 | 6/2016 |
| WO | 2018067683 A1 | 4/2018 |

OTHER PUBLICATIONS

Perera Wilmer H et al, "Rebaudiosides T and U, minor C-19 xylopyranosyl and arabinopyranosyl steviol glycoside derivatives fromStevia rebaudiana(Bertoni) Bertoni", Phytochemistry, (Dec. 12, 2016), vol. 135, doi:10.1016/J.PHYTOCHEM.2016.12.001, ISSN 0031-9422, pp. 106-114, XP029898124 [XP] 1,2.
Venkata Sai Prakash Chaturvedula et al, "Minor diterpenoid glycosides from the leaves of Stevia rebaudiana", Phytochemistry Letters, Elsevier, Amsterdam, NL, vol. 4, No. 3, doi:10.1016/J.PHYTOL. 2011.01.002, ISSN 1874-3900, (Jan. 24, 2011), pp. 209-212, (Jan. 31, 2011), XP028299085 [X] 1,2.
Starratt A N et al, "Rebaudioside F, a diterpene glycoside from Stevia rebaudiana", Phytochemistry, Elsevier, Amsterdam, NL, (Feb. 1, 2002), vol. 59, No. 4, doi:10.1016/S0031-9422(01)00416-2, ISSN 0031-9422, pp. 367-370, XP004335033 [X] 1,2.
Chaturvedula Venkata Sai Prakash et al, "Two minor diterpene glycosides from the leaves of Stevia rebaudiana", vol. 6, No. 2, doi:10.1177/1934578X1100600205, ISSN 1934-578X, (Jan. 31, 2011), pp. 175-178, Natural Product Communications, Natural Product Inc, US, URL: http://journals.sagepub.com/doi/pdf/10.1177/1934578X1100600205, (Feb. 1, 2011), XP009523297 [X] 1,2.
Mohamed A. Ibrahim et al, "Rebaudiosides R and S, Minor Diterpene Glycosides from the Leaves of Stevia rebaudiana", Journal of Natural Products, US, (Apr. 27, 2016), vol. 79, No. 5, doi:10.1021/acs.jnatprod.6b00048, ISSN 0163-3864, pp. 1468-1472, XP055736842 [X] 1,2.
Mohamed A. Ibrahim et al, "Minor Diterpene Glycosides from the Leaves of Stevia rebaudiana", Journal of Natural Products, US, (Apr. 23, 2014), vol. 77, No. 5, doi:10.1021/np4009656, ISSN 0163-3864, pp. 1231-1235, XP055340471 [X] 1,2.
Douglas L. Rodenburg et al, "Development of HPLC Analytical Techniques for Diterpene Glycosides from Stevia rebaudiana (Bertoni) Bertoni: Strategies to Scale-up", Journal of the Brazilian Chemical Society, São Paulo; BR, (Mar. 18, 2016), doi:10.5935/0103-5053. 20160082, ISSN 0103-5053, XP055736864 [X] 1,2.

(Continued)

Primary Examiner — Dale R Miller

(57) ABSTRACT

A purified composition of steviol glycoside molecules is described. The composition imparts desirable taste, flavor and flavor modifying properties to food, beverages, and other consumable products.

2 Claims, 28 Drawing Sheets

(56) References Cited

OTHER PUBLICATIONS

Pubchem, (Oct. 26, 2006), Database accession No. 11088897 [A] 1-2.
Kuo, et al., "New Dammarane-Type Saponins from the Galls of Sapindus Mukorossi", J. Agric. Food Chem, vol. 53, pp. 4722-4727, Year 2015.

\* cited by examiner

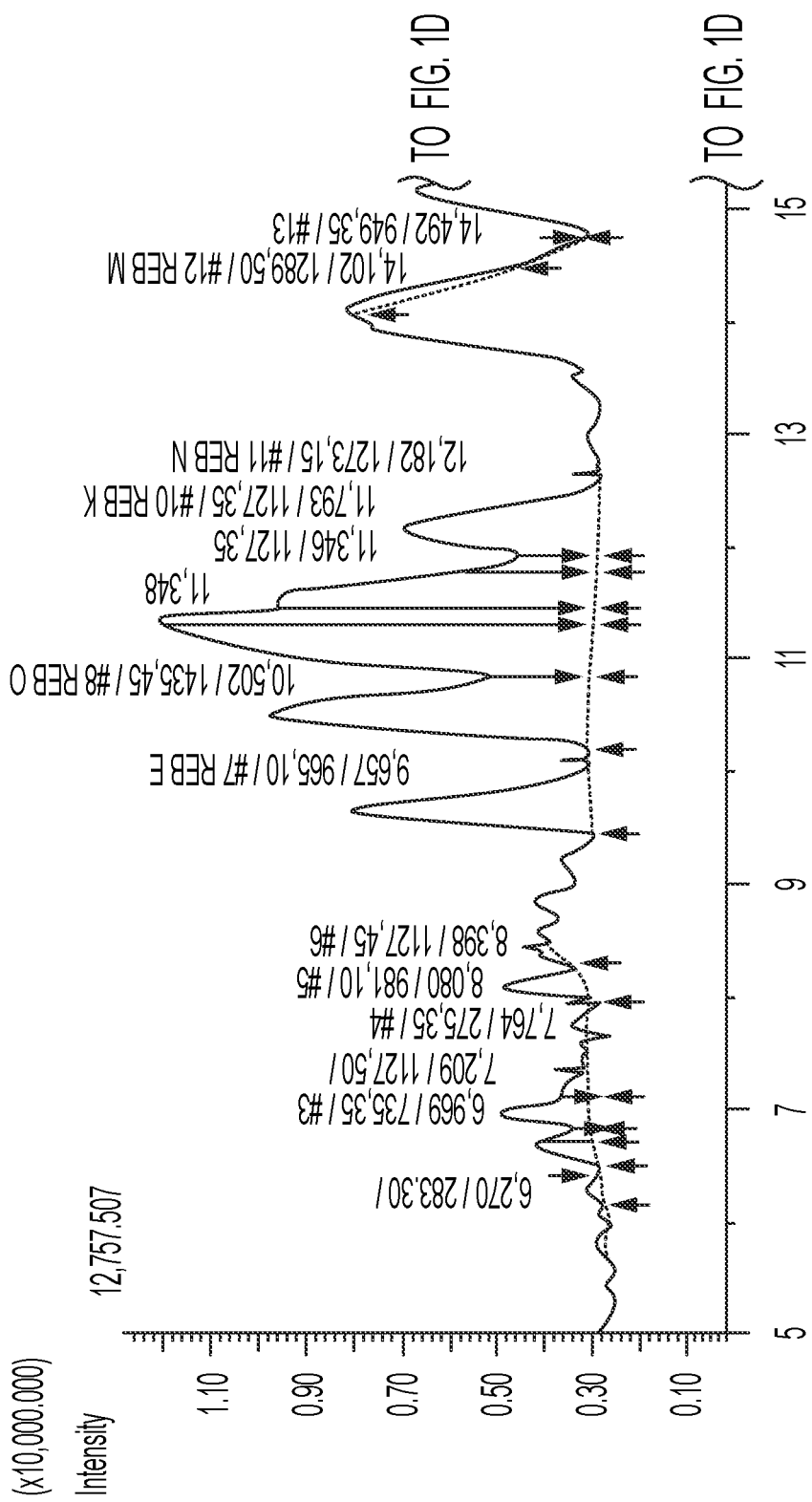

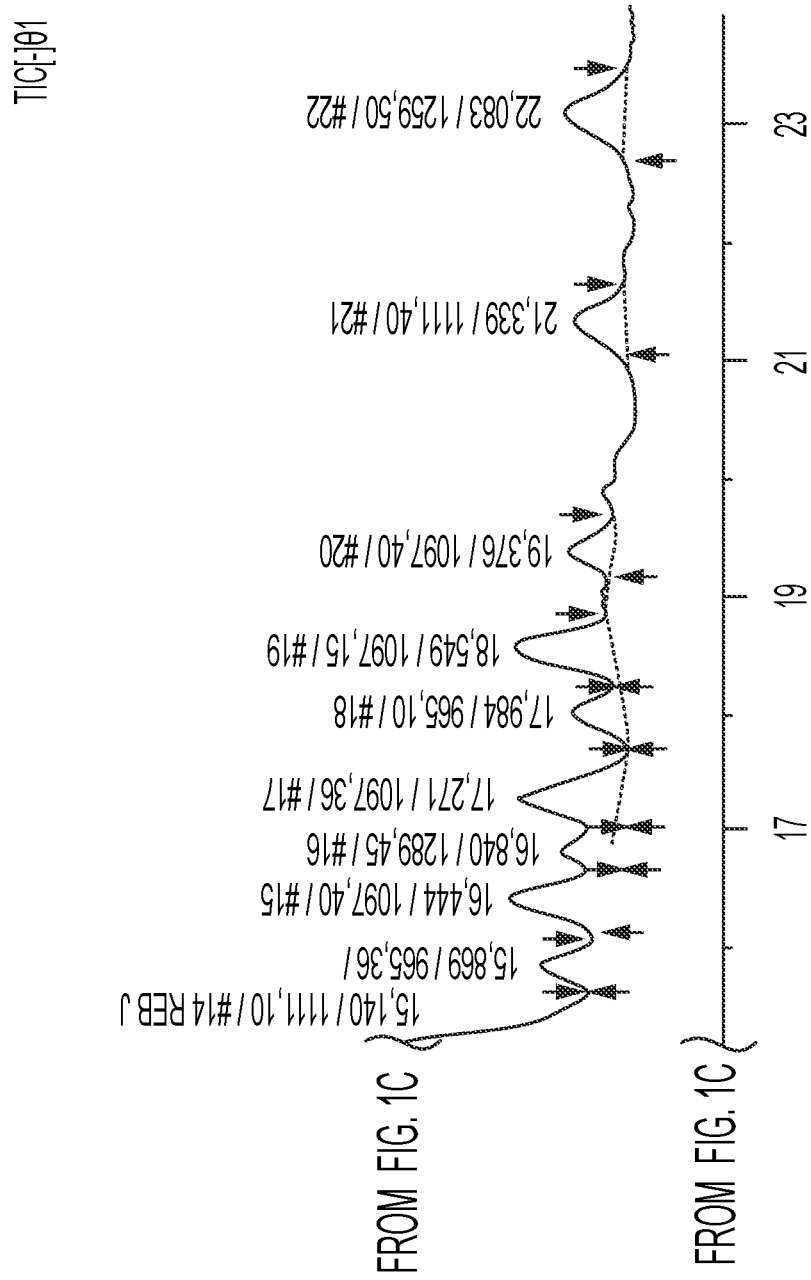

Representative analytical chromatogram of stevia extract A95 using Gradient KM7. MS TIC(-) (top, middle), ELSD chromatogram (bottom)

Fig. 4- RSG1 (#1)

1

Chemical Formula: $C_{21}H_{30}O_{11}$
Exact Mass: 458,1788
Molecular Weight: 458,4563

Figure 5: RSG2 (#2)

Figure 6: RSG3 (#3)

Chemical Formula: $C_{32}H_{52}O_{15}$
Exact Mass: 676,3306
Molecular Weight: 676,7463

Figure 7: RSG4 (#4)

4
Chemical Formula: $C_{50}H_{80}O_{28}$
Nominal mass: 1129.2

Figure 8: RSG5 (#5)

5
Chemical Formula: $C_{44}H_{70}O_{24}$
Nominal mass: 983.0

Figure 9: RSG6 (#18)

18
Chemical Formula: $C_{44}H_{70}O_{23}$
Nominal mass: 967.0

Rebaudioside T (#6)*

6
Chemical Formula: $C_{50}H_{80}O_{28}$
Exact Mass: 1128.4836
Molecular Weight: 1129.1534

Rebaudioside Y (#ACD2)

Rebaudioside O2 (#ACD14)

ACD14
Chemical Formula: $C_{62}H_{100}O_{37}$
Nominal mass: 1437.4

Rebaudioside C2 (#13)

13

Chemical Formula: $C_{44}H_{70}O_{22}$
Exact Mass: 950.4359
Molecular Weight: 951.0134

Rebaudioside W (#15)*

15

Chemical Formula: $C_{49}H_{78}O_{27}$
Exact Mass: 1098.4730
Molecular Weight: 1099.1274

Rebaudioside W2 (#17b)

17b

Chemical Formula: $C_{49}H_{78}O_{27}$
Exact Mass: 1098.4730
Molecular Weight: 1099.1274

Rebaudioside U2 (#17a)

Preparative RP-HPLC chromatogram of 3.85 g of enriched minor compounds. Fractions 51+52 are marked by a rectangle ELSD chromatogram (top) of fractions 66+67 and MS spectrum (bottom) of compound #19 with $t_R$ = 20.5 min Rebaudioside W3 (#19)

Rebaudioside V (#ACD6)

ACD6
Chemical Formula: $C_{55}H_{88}O_{32}$
Nominal mass: 1261.3

Rebaudioside U (#20)

20

Chemical Formula: $C_{49}H_{78}O_{27}$
Exact Mass: 1098.4730
Molecular Weight: 1099.1274

Rebaudioside K2 (#21)

21

Chemical Formula: $C_{50}H_{80}O_{27}$
Exact Mass: 1112.4887
Molecular Weight: 1113.1540

Rebaudioside V2 (#22)

22

Chemical Formula: $C_{55}H_{88}O_{32}$
Exact Mass: 1260.5259
Molecular Weight: 1261.2680

STEVIA-DERIVED MOLECULES, METHODS OF OBTAINING SUCH MOLECULES, AND USES OF THE SAME

BACKGROUND OF THE INVENTION

Sugar alternatives are receiving increasing attention due to awareness of many diseases in conjunction with consumption of high-sugar foods and beverages. However, many artificial sweeteners such as dulcin, sodium cyclamate and saccharin were restricted in some countries due to debatable concerns on their safety. Therefore, non-caloric sweeteners of natural origin are becoming increasingly popular. The sweet herb *Stevia rebaudiana* produces a number of diterpene glycosides which feature high intensity sweetness and sensory properties superior to those of many other high potency sweeteners.

*Stevia rebaudiana* is a plant species belonging to the Astracea family, and is native to South America and cultivated now in many parts of the world (Gardana et al., 2003; Koyama et al., 2003; Carakostas et al., 2008). *Stevia* leaves are naturally sweet, and have been used for sweetening food products for hundreds of years in South America (Soejarto et al., 1982). Extracts of *Stevia rebaudiana* have been used commercially to sweeten foods in Japan and other Southeast Asian countries for a number of years (Koyama et al., 2003). As a product of nature, the *stevia* plant leaves contain different sweet tasting components, called steviol glycosides. Reportedly, more than 40 steviol glycosides have been identified that are typically present in the *stevia* leaf extract (Ceunen and Geuns, 2013; Purkayastha et al, 2016). Each of these steviol glycosides has its own unique taste profile and sweetness intensity, which can be up to 350 times sweeter than sugar, but all share a similar molecular structure where different sugar moieties are attached to aglycone steviol (an ent-kaurene-type diterpene).

The leaves of the *Stevia* plant contain a mixture containing diterpene glycosides in an amount ranging from about 10% to 20% of the total dry weight. These diterpene glycosides are about 30 to 450 times sweeter than sugar. Structurally, many of the diterpene glycosides are characterized by a single base, steviol, and differ by the presence of carbohydrate residues at positions C13 and C19. Typically, on a dry weight basis, the four major steviol glycosides found in the leaves of *Stevia* are dulcoside A (0.3%), rebaudioside C (0.6-1.0%), rebaudioside A (3.8%) and stevioside (9.1%). Other glycosides identified in *Stevia* extract include rebaudioside B, D, E, and F, steviolbioside and rubusoside.

Rebaudioside A and stevioside have garnered the most commercial interest and have been extensively studied and characterized in terms of their suitability as commercial high intensity sweeteners. Stability studies in carbonated beverages confirmed their heat and pH stability (Chang S. S., Cook, J. M. (1983) Stability studies of stevioside and rebaudioside A in carbonated beverages. J. Agric. Food Chem. 31: so 409-412.)

Steviol glycosides differ from each other not only by molecular structure, but also by their taste properties. Usually stevioside is found to be 110-270 times sweeter than sucrose and rebaudioside A is between 150 and 320 times sweeter than sucrose. Rebaudioside A has the least astringent, the least bitter, and the least persistent aftertaste thus possessing the most favorable sensory attributes in major steviol glycosides (Tanaka O. (1987) Improvement of taste of natural sweeteners. Pure Appl. Chem. 69:675-683; Phillips K. C. (1989) *Stevia*: steps in developing a new sweetener. In: Grenby T. H. ed. Developments in sweeteners, vol. 3. Elsevier Applied Science, London. 1-43.)

By the early 21st century, only a limited number of the chemical structures of steviol glycosides in *Stevia rebaudiana* have been characterized including stevioside, rebaudioside A-F, dulcoside A, and steviolbioside (Ceunen and Geuns, 2013). In recent years, many minor steviol glycosides with diverse chemical structures, have been reported from the leaves of *Stevia rebaudiana* (Chaturvedula et al., 2011a,b,c; Chaturvedula and Prakash, 2011 a,b). These diverse steviol glycosides, which are ent-kaurene-type diterpenes, are connected to various sugars such as glucose, rhamnose, xylose, fructose and deoxy glucose at C-13 and C-19 positions via 1,2-; 1,3-; 1,4- or 1,6-α or β-glycosidic linkages (Purkayastha et al, 2016).

The use of steviol glycosides has been limited to date by certain undesirable taste properties, including licorice taste, bitterness, astringency, sweet aftertaste, bitter aftertaste, licorice aftertaste, and become more prominent with increase of concentration. These undesirable taste attributes are particularly prominent in carbonated beverages, where full replacement of sugar requires concentrations of steviol glycosides that exceed 600 mg/L. Use of steviol glycosides in such high concentrations results in significant deterioration in the final product taste.

Accordingly, there remains a need to develop natural reduced or non-caloric sweeteners that provide a temporal and flavor profile similar to the temporal and flavor profile of sucrose.

There remains a further need for methods for purifying glycosides from *stevia* plants.

SUMMARY OF THE INVENTION

The present invention relates generally to novel diterpene glycosides and compositions and consumables comprising said novel diterpene glycosides, as well as methods for purifying said novel diterpene glycosides, methods for preparing compositions and consumables comprising said novel diterpene glycosides and methods for enhancing or modifying the flavor or sweetness of consumables using the novel diterpene glycosides. The novel diterpene glycosides of the present invention are isolated from *Stevia* plants.

The present invention is directed to *stevia*-derived molecules, methods for obtaining such molecules, and uses of such molecules. These *stevia*-derived molecules may or may not have the steviol backbone structure, but have structures that may be somewhat or substantially similar to steviol glycosides. In some cases, these molecules have structures that are very different from steviol glycosides. These *stevia*-derived molecules have desirable taste and flavor properties, which may include sweetness imparting properties, flavor modifying properties, a combination of these properties, and other properties.

DETAILED DESCRIPTION

The chemical structures of certain of the *stevia*-derived molecules of the present invention are shown in the Figures appended hereto. As used herein, "*stevia*-derived molecules" shall refer to molecules obtained from any part of the plants of any variety of the species *Stevia rebaudiana*.

These *stevia*-derived molecules are useful in the preparation of food, beverages, nutraceuticals, pharmaceuticals, tobacco products, cosmetics, oral hygiene products, and the like. Some of the *stevia*-derived molecules have a steviol backbone, and may be referred to as steviol glycosides. Other *stevia*-derived molecules of this invention have a different backbone, but may have properties similar to steviol glycosides, or may have other beneficial properties.

These *stevia*-derived molecules can be used alone or in combination with other ingredients, such as sweeteners, flavors, flavor modifiers, and the like. Such other ingredients may include steviol glycoside ingredients, or ingredients from other natural or synthetic sources.

Methods of obtaining *stevia*-derived molecules include the methods used to extract steviol glycosides from *Stevia* plant leaves. Other methods may include extraction from other parts of the plant, or other extraction techniques and solvents.

The following Example demonstrates certain embodiments of the invention, and is not intended to limit the scope of the invention in any way.

Example 1

A *stevia* extract available from PureCircle USA Inc. of Oak Brook, IL, labeled as "A95", was used to isolate and characterize major and minor steviol glycoside components using the following analytical methodologies.

1.1 Sample
Product Name: *Stevia* leaf extract A95
Batch No.: WIP A95 27A
Manufacturing date: 2 Apr. 2016

1.2 Analytical LCMS (Liquid Crystal Mass Spectrometry)
Analytical LCMS was performed on a Shimadzu single quad UPLC-system (see Table 1). Two different gradient systems were applied (see Tables 2a and 2b) which are identical for the first 40 min. Gradient KM7 was used to resolve all compounds including already identified steviol glycosides #25-#29, while gradient ACD1 was faster and used for the analysis of compounds #1-#24.

Reference samples were prepared by dissolving *Stevia* leaf extract A95 (20 mg) in a 1:1 mixture of methanol and dimethyl sulfoxide (DMSO). Sonification for 30 min was necessary to achieve a homogenous solution. The solution was stored at 4° C.

The analytical system proved to be very sensitive towards changes in solvent composition and retention time shifts were observed when a new batch of solvents was used. Therefore, reference samples were analyzed before and after every analytical batch and the assignment of retention times was verified.

Figure 1A:
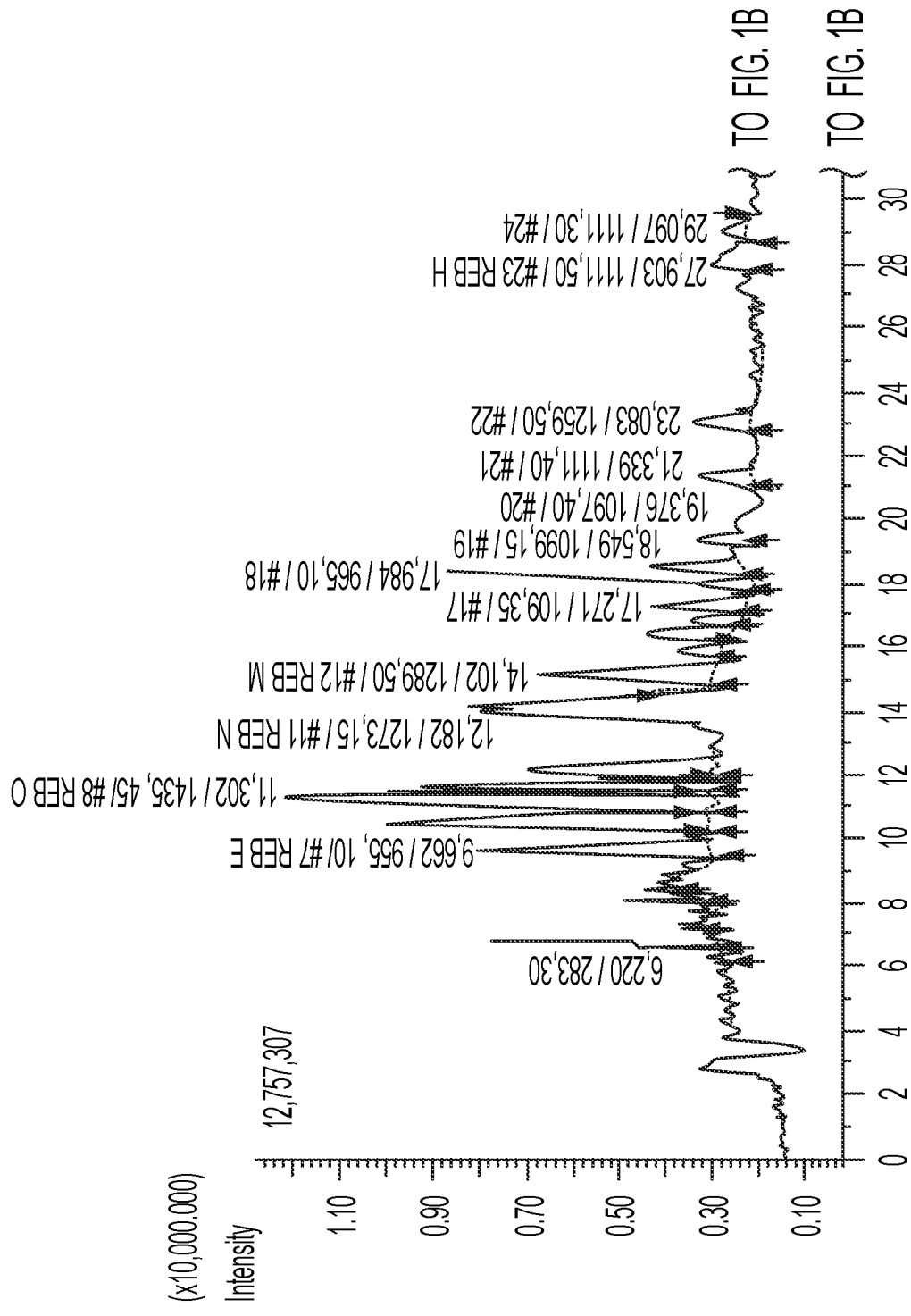
FIG. 1 shows a representative analytical chromatogram of *stevia* extract A95 using Gradient KM7. The top and middle plots are MS TIC(−) (mass spectrometry total ion current) chromatograms, and the bottom plot is an ELSD (evaporative light scattering detector) chromatogram.
Figure 1B:
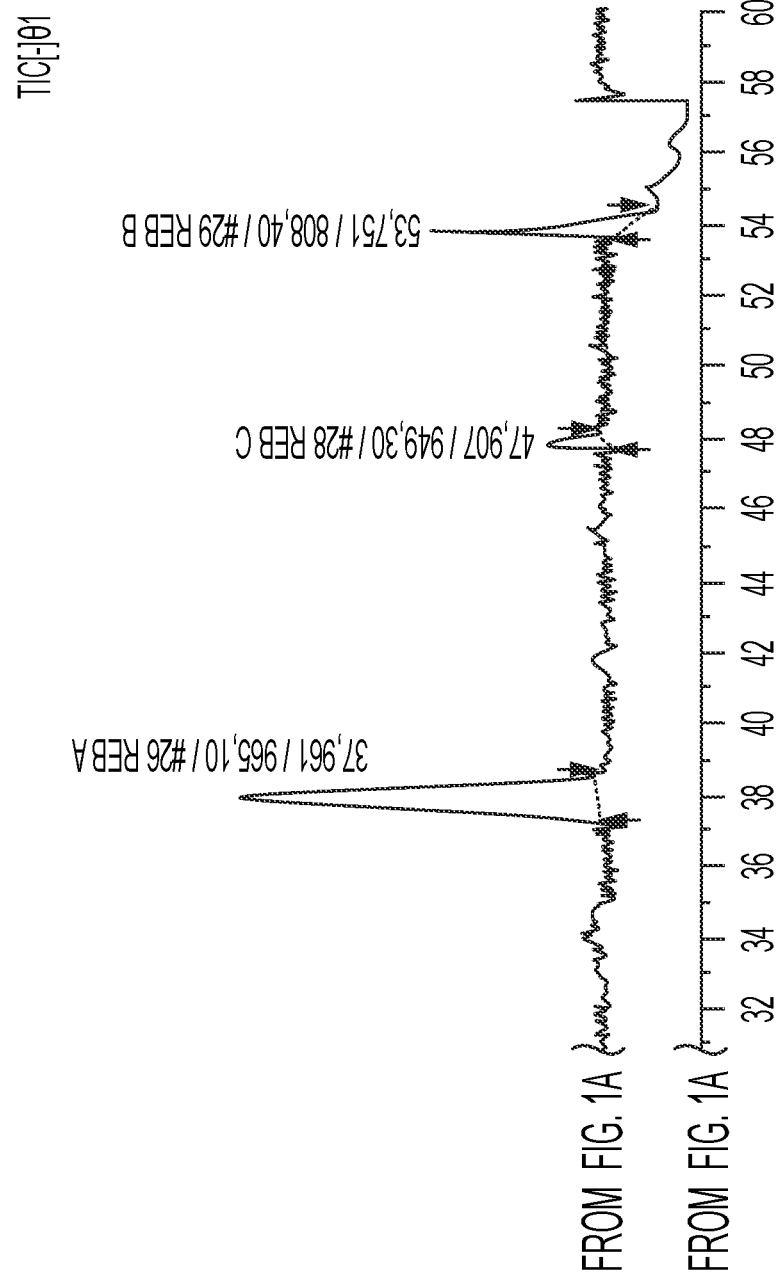
Figure 1E:
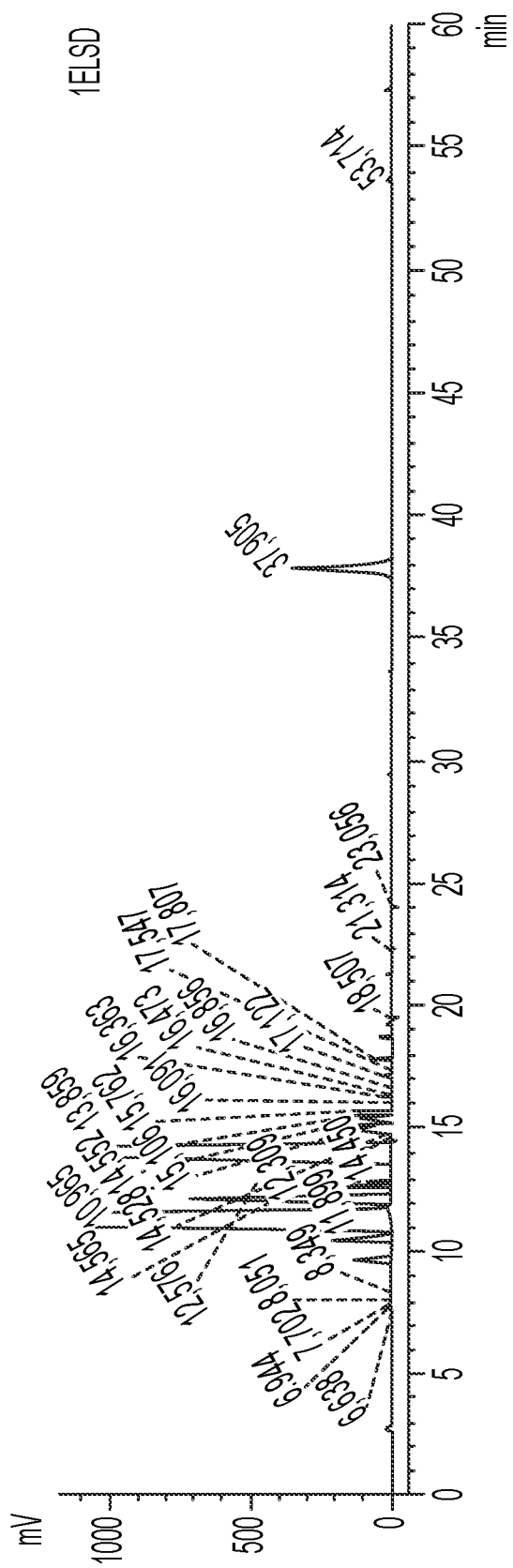

A typical analytical chromatogram using gradient KM7 is shown in FIG. 1.

TABLE 1

| LCMS system | |
|---|---|
| HPLC System | Shimadzu LC-30AD, prominence |
| Interface | Shimadzu CBM-20A |
| Degasser | Shimadzu DGU-20A5 |
| Autosampler | Shimadzu SIL-30AC, prominence |
| Column oven | Shimadzu CTO-20AC |
| MS | Shimadzu 2020 Single quadrupole |
| DAD | Shimadzu SPD-M20A |
| ELSD | Sedere ELSD-LT II, Sedex 85 |
| Stationary Phase | Agilent Poroshell 120 SB-C18 2.7 µm, 4.6 × 150 mm |
| Flow Rate | 0.5 mL/min |
| Mobile Phase: | A: Water, 25% Acetonitrile, 0.2% Acetic acid B: Acetonitrile |

TABLE 2

| LCMS Gradients | | | | |
|---|---|---|---|---|
| Gradient KM7 | Time [min] | A [%] | B [%] | Flow [ml/min] |
| | 00.00 | 100 | 0 | 0.5 |
| | 24.00 | 100 | 0 | 0.5 |
| | 50.00 | 90 | 10 | 0.5 |
| | 51.00 | 0 | 100 | 0.5 |
| | 55.00 | 0 | 100 | 0.5 |
| | 56.00 | 100 | 0 | 0.5 |
| | 56.01 | 100 | 0 | 1.0 |
| | 65.00 | 100 | 0 | 0.5 |
| | 70.00 | 100 | 0 | 0 |
| Gradient ACD1 | Time [min] | A [%] | B [%] | Flow [ml/min] |
| | 00.00 | 100 | 0 | 0.5 |
| | 24.00 | 100 | 0 | 0.5 |
| | 40.00 | 94.6 | 5.4 | 0.5 |
| | 41.00 | 0 | 100 | 0.5 |
| | 45.00 | 0 | 100 | 0.5 |
| | 46.00 | 100 | 0 | 0.5 |
| | 46.01 | 100 | 0 | 1.0 |
| | 55.00 | 100 | 0 | 0.5 |
| | 60.00 | 100 | 0 | 0 |

1.3 Recrystallisation

*Stevia* leaf extract A95 (100 g, white powder) were dissolved in ethanol/water 70/30 (750 mL) at a temperature of 65° C.
The milky solution was allowed to cool down to room temperature in a water bath and then filtrated through a suction filter. The collected crystals were washed with ethanol, dried and stored. Mother liquor and wash solution were kept separate and the respective solvent was removed under vacuum.

1.4 Reversed Phase MPLC (Medium Pressure Liquid Chromatography)

The respective sample (15 g) is dissolved in methanol, celite (30 g) is added and the solvent removed by a rotary evaporator. The immobilized sample is transferred into a glass column and built into the MPLC system described in Table 3. A time based fractionation leads to 18 fractions (4 min each). Solvents and gradients are described in Table 3.

TABLE 3

MPLC-System and gradients

| Pump System | | | | | | |
|---|---|---|---|---|---|---|
| Interface Module | SCPA | | | | | |
| Fraction collector | Labomatic Labocol Vario 2000 plus | | | | | |
| Stationary Phase | Polygoprep C18, 50-60 µm, glas column 50 × 250 mm | | | | | |

| Mobile Phase: | A: Water B: Aceton | | | C: Methanol D: 2-Propanol | | |
|---|---|---|---|---|---|---|
| | Time [min] | A [%] | B [%] | C [%] | D [%] | Flow [ml/min] |
| Gradient A | 00.00 | 85 | 15 | 0 | 0 | 90 |
| | 51.00 | 65 | 35 | 0 | 0 | 90 |
| | 56.00 | 0 | 0 | 100 | 0 | 90 |
| | 61.00 | 0 | 0 | 0 | 100 | 90 |

| Mobile Phase: | A: Water B: Methanol | | | C: Methanol D: 2-Propanol | | |
|---|---|---|---|---|---|---|
| | Time [min] | A [%] | B [%] | C [%] | D [%] | Flow [ml/min] |
| Gradient B | 00.00 | 75 | 25 | 0 | 0 | 90 |
| | 51.00 | 50 | 50 | 0 | 0 | 90 |
| | 56.00 | 0 | 0 | 100 | 0 | 90 |
| | 61.00 | 0 | 0 | 0 | 100 | 90 |

1.5 Normal Phase Chromatography

The respective sample (20 g) is dissolved in methanol, silica (40 g) is added and the solvent removed by a rotary evaporator. The immobilized sample is transferred into a glass column and built into the high pressure liquid chromatography (HPLC) system described in Table 4. Air is removed from the transfer column by washing with Ethyl acetate/methanol 1:1. A time based fractionation leads to 90 fractions (0.5 min each) which are combined based on the UV and ELSD data generated during fractionation. Resulting fractions are analyzed by LCMS. Solvents and gradients are described in Table 4.

TABLE 4

Preparative HPLC System 2 (HTP-II, NP-Fractionation)

| HPLC System | Knauer K-1800 |
|---|---|
| Autosampler | Merck L-7250 |
| UV-detector | Knauer |
| ELSD | Biotage ELSD-A120 |
| Fraction collector | Merck L-7650 |
| Stationary Phase | Silica, 50-60 µm |

TABLE 4-continued

Preparative HPLC System 2 (HTP-II, NP-Fractionation)

| Mobile Phase | A: Aceton/Ethyl acetate/Water (50/40/10); B: Aceton/Ethyl acetate (85/15) | | | |
|---|---|---|---|---|
| | Time [min] | A [%] | B [%] | Flow [ml/min] |
| Gradient A | 00.00 | 100 | 0 | 35 |
| | 372.00 | 0 | 100 | 35 |

1.6 Reversed Phase HPLC

The respective sample (up to 3.5 g) is dissolved in methanol, C-18 RP material is added and the solvent removed by a rotary evaporator. The immobilized sample is transferred into a column and built into the HPLC system described in Table 5. A time based fractionation leads to 120 fractions (27 sec each) which are combined based on the UV and ELSD data generated during fractionation. Resulting fractions are analyzed by LCMS. Solvents and gradients are described in Table 5.

TABLE 5

Preparative HPLC System 3 (SEPbox)

| HPLC System | Sepiatec SEPbox lite | | |
|---|---|---|---|
| UV-detector | Merck L-7400 | | |
| ELSD | Sedere Sedex 75 | | |
| Fraction collector | Merck L-7650 | | |
| Stationary Phase | Lichrospher Select B, 10 µm 50 × 250 mm | | |
| Mobile Phase | A: Water, ammonium formate (5 mmol), formic acid, pH 3 B: Methanol/Acetonitril (1/1), ammonium formate (5 mmol), formic acid, pH 3 | | |
| Delay before fractionation | 215 sec | Fraction | 29 sec |
| | Time [min] | A [%] | B [%] | Flow [ml/min] |
| Gradient A | 00.00 | 72 | 28 | 80 |
| | 57.7 | 46 | 54 | 80 |

TABLE 5-continued

Preparative HPLC System 3 (SEPbox)

| | | | |
|---|---|---|---|
| 58 | 0 | 100 | 80 |
| 105 | 0 | 100 | 80 |

| Stationary Phase | Kromasil C18, 10 µm 25 × 250 mm |
|---|---|
| Mobile Phase | A: Water, ammonium formate (5 mmol), formic acid, pH 3 |
| | B: Methanol, ammonium formate (5 mmol), formic acid, pH 3 |
| Delay before fractionation | 215 sec   Fraction   29 sec |

| Gradient B | Time [min] | A [%] | B [%] | Flow [ml/min] |
|---|---|---|---|---|
| | 00.00 | 61 | 39 | 30 |
| | 57.7 | 43 | 57 | 30 |
| | 58 | 0 | 100 | 30 |
| | 105 | 0 | 100 | 30 |

| Stationary Phase | Lichrospher Select B, 10 µm 50 × 250 mm |
|---|---|
| Mobile Phase | A: Water, ammonium formate (5 mmol), formic acid, pH 3 |
| | B: Methanol/Acetonitril (1/1), ammonium formate (5 mmol), formic acid, pH 3 |
| Delay before fractionation | 215 sec   Fraction   29 sec |

| Gradient C | Time [min] | A [%] | B [%] | Flow [ml/min] |
|---|---|---|---|---|
| | 00.00 | 70 | 30 | 80 |
| | 57.7 | 62 | 38 | 80 |
| | 58 | 0 | 100 | 80 |
| | 105 | 0 | 100 | 80 |

| Stationary Phase | Lichrospher Select B, 10 µm 50 × 250 mm |
|---|---|
| Mobile Phase | A: Water, ammonium formate (5 mmol), formic acid, pH 3 |
| | B: Methanol/Acetonitril (1/1), ammonium formate (5 mmol), formic acid, pH 3 |
| | 215 sec |
| Delay before fractionation | 215 sec   Fraction   29 sec |

| Gradient D | Time [min] | A [%] | B [%] | Flow [ml/min] |
|---|---|---|---|---|
| | 00.00 | 68 | 32 | 80 |
| | 57.7 | 53 | 47 | 80 |
| | 58 | 0 | 100 | 80 |
| | 105 | 0 | 100 | 80 |

| Stationary Phase | Kromasil C18, 10 µm 50 × 250 mm |
|---|---|
| Mobile Phase | A: Water, formic acid 0.1%, pH 3 |
| | B: Acetonitril, formic acid 0.1%, pH 3 |
| Delay before fractionation | 180 sec   Fraction   22 sec |

| Gradient E | Time [min.sec] | A [%] | B [%] | Flow [ml/min] |
|---|---|---|---|---|
| | 00.00 | 76 | 24 | 109 |
| | 40.50 | 70 | 30 | 109 |
| | 41.00 | 0 | 100 | 109 |
| | 45.00 | 0 | 100 | 109 |

| Stationary Phase | Kromasil C18, 10 µm 25 × 250 mm |
|---|---|
| Mobile Phase | A: Water, ammonium formate (5 mmol), formic acid, pH 3 |
| | B: Methanol, ammonium formate (5 mmol), formic acid, pH 3 |
| Delay before fractionation | 180 sec   Fraction   22 sec |

| Gradient F | Time [min] | A [%] | B [%] | Flow [ml/min] |
|---|---|---|---|---|
| | 00.00 | 46 | 54 | 47 |
| | 40.50 | 38 | 62 | 47 |
| | 41.00 | 0 | 100 | 47 |
| | 45.00 | 0 | 100 | 47 |

TABLE 5-continued

Preparative HPLC System 3 (SEPbox)

| Stationary Phase | Lichrospher Select B, 10 µm 50 × 250 mm |
|---|---|
| Mobile Phase | A: Water, ammonium formate (5 mmol), formic acid, pH 3 |
| | B: Methanol/Acetonitril (1/1), ammonium formate (5 mmol), formic acid, pH 3 |
| Delay before fractionation | 215 sec   Fraction   29 sec |

| Gradient G | Time [min] | A [%] | B [%] | Flow [ml/min] |
|---|---|---|---|---|
| | 00.00 | 70 | 30 | 80 |
| | 57.7 | 55 | 45 | 80 |
| | 58 | 0 | 100 | 80 |
| | 105 | 0 | 100 | 80 |

| Stationary Phase | Kromasil C18, 10 µm 25 × 250 mm |
|---|---|
| Mobile Phase | A: Water, ammonium formate (5 mmol), formic acid, pH 3 |
| | B: Methanol, ammonium formate (5 mmol), formic acid, pH 3 |
| Delay before fractionation | 180 sec   Fraction   22 sec |

| Gradient H | Time [min] | A [%] | B [%] | Flow [ml/min] |
|---|---|---|---|---|
| | 00.00 | 50 | 50 | 47 |
| | 40.50 | 49 | 61 | 47 |
| | 41.00 | 0 | 100 | 47 |
| | 45.00 | 0 | 100 | 47 |

| Stationary Phase | Kromasil C18, 10 µm 50 × 250 mm |
|---|---|
| Mobile Phase | A: Water, formic acid 0.1%, pH 3 |
| | B: Acetonitril, formic acid 0.1%, pH 3 |
| Delay before fractionation | 180 sec   Fraction   22 sec |

| Gradient K | Time [min.sec] | A [%] | B [%] | Flow [ml/min] |
|---|---|---|---|---|
| | 00.00 | 78 | 22 | 109 |
| | 40.50 | 68 | 32 | 109 |
| | 41.00 | 0 | 100 | 109 |
| | 45.00 | 0 | 100 | 109 |

| Stationary Phase | Kromasil C18, 10 µm 50 × 250 mm |
|---|---|
| Mobile Phase | A: Water, formic acid 0.1%, pH 3 |
| | B: Acetonitril, formic acid 0.1%, pH 3 |
| Delay before fractionation | 180 sec   Fraction   22 sec |

| Gradient L | Time [min.sec] | A [%] | B [%] | Flow [ml/min] |
|---|---|---|---|---|
| | 00.00 | 75 | 25 | 109 |
| | 40.50 | 68 | 32 | 109 |
| | 41.00 | 0 | 100 | 109 |
| | 45.00 | 0 | 100 | 109 |

1.7 HILIC (Hydrophilic Interaction Liquid Chromatography)

The respective sample is dissolved in 2 mL of a 3:1 mixture of solvents A and B (see Table 6). Sample Injection takes place after 9.95 min. A time based fractionation leads to 96 fractions (43 sec each, starting after 18 min) which are combined based on the UV and ELSD data generated during fractionation. Resulting fractions are analyzed by LCMS. Solvents and gradients are described in Table 6.

TABLE 6

Preparative HPLC System 1 (HTP-I, HILIC-Fractionation)

| HPLC System | Knauer K-1800 |
|---|---|
| Autosampler | Merck L-7250 |
| UV-detector | Knauer |
| ELSD | ELSD Sedex 75 |

TABLE 6-continued

Preparative HPLC System 1 (HTP-I, HILIC-Fractionation)

| | |
|---|---|
| Fraction collector | Merck L-7650 |
| Stationary Phase | Kromasil 60-10-HILIC-D 50 × 250 mm |
| Flow Rate | 80 mL/min |
| Mobile Phase: | A: Acetonitril; 0.1% Acetic acid; |
| | B: Methanol/Water/Acetic acid (95/4.9/0.1) |

| Gradient | Time [min] | % A | % B | Flow [ml/min] |
|---|---|---|---|---|
| | 00.00 | 75 | 25 | 80 |
| | 11.50 | 75 | 25 | 80 |
| | 65.00 | 65 | 35 | 80 |
| | 70.00 | 0 | 100 | 80 |
| | 75.00 | 0 | 100 | 80 |

1.8 NMR (Nuclear Magnetic Resonance)

Isolated compounds were identified by NMR spectroscopy using a Bruker 500 Mhz NMR spectrometer. Identification of the aglycon was based on reference $^1$H-NMR spectra using C17, C18 and C20 proton signals as primary indicators. Especially C20 proton shifts indicated alterations as seen in compounds #4 and #18. Glycosides were elucidated using H-H-Cosy, HSQC and HMBC and experiments using spectra of literature known steviosides as reference.

1.9 Results

Figure 2:
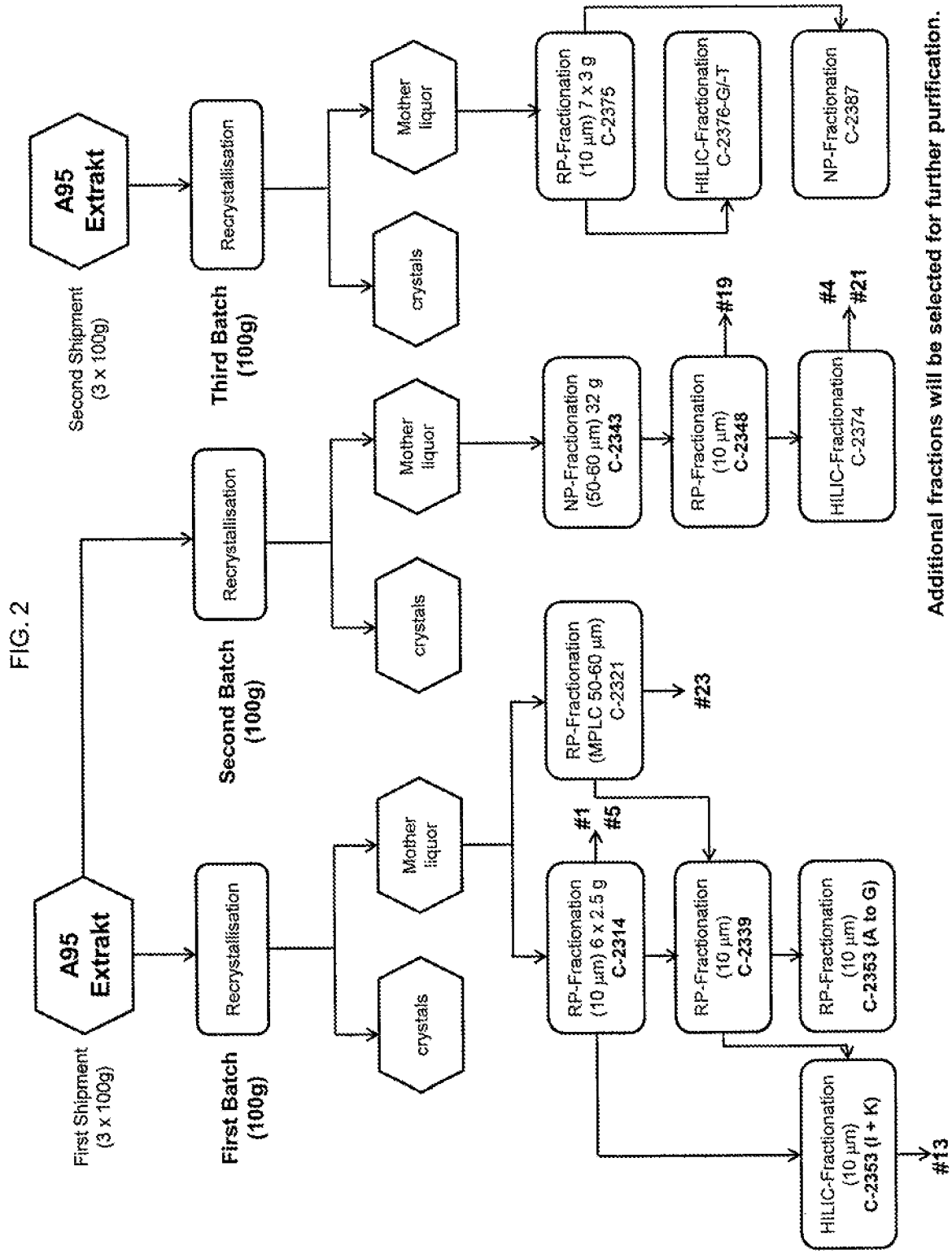
FIG. 2 is a chart of the schematic steps used to isolate different compounds listed in Table 1.
Figure 3:
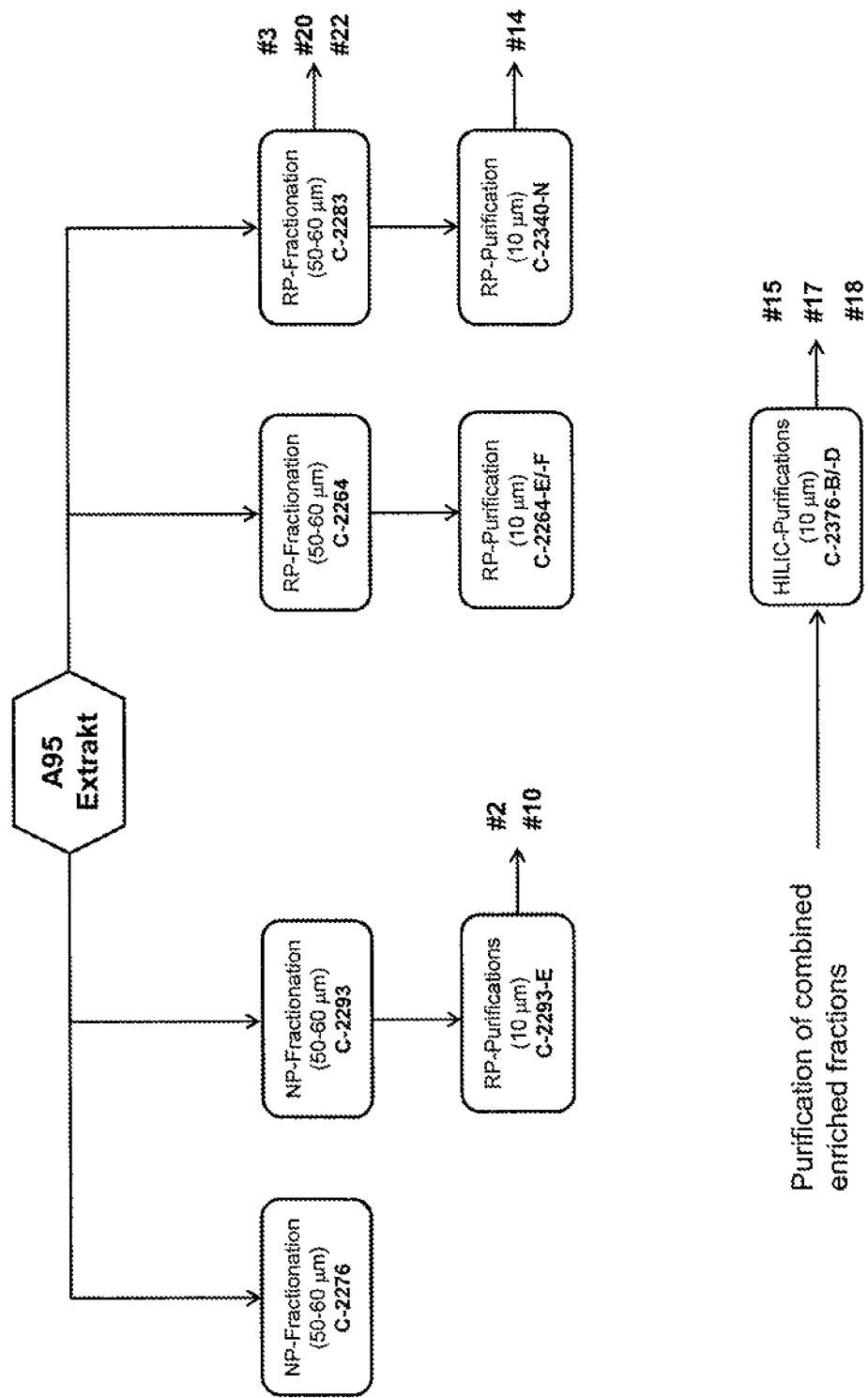
FIG. 3 is a chart of the schematic steps used to isolate different compounds listed in Table 1.
Figure 4:
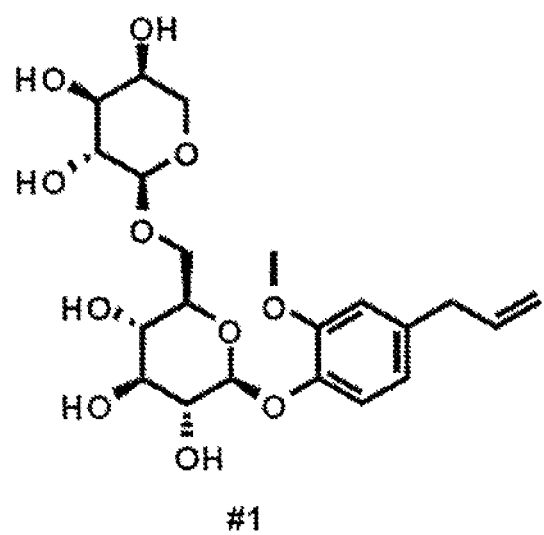
FIG. 4 shows the structure of RSG1 (Related Steviol Glycoside 1).
Figure 5:
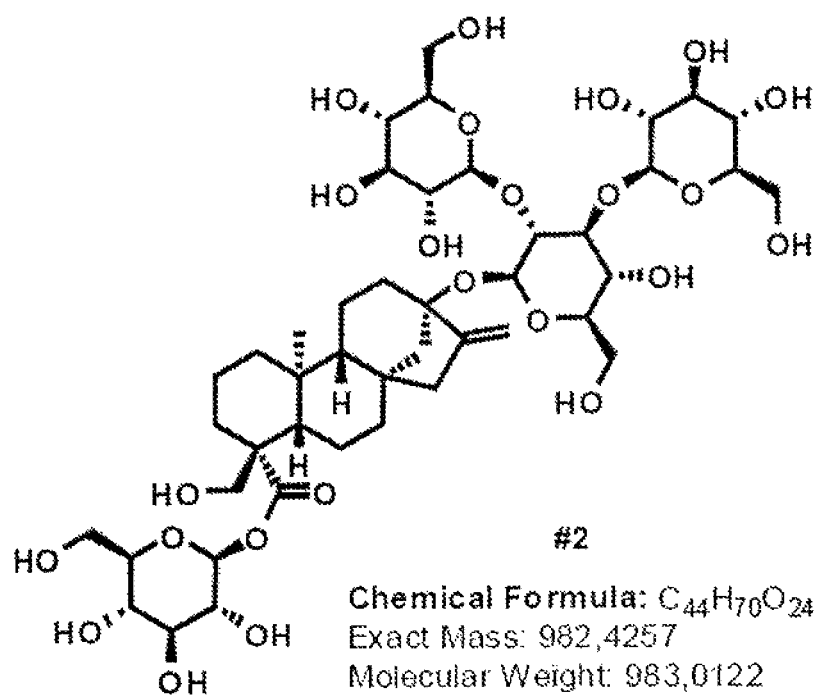
FIG. 5 shows the structure of RSG2 (Related Steviol Glycoside 2).
Figure 6:
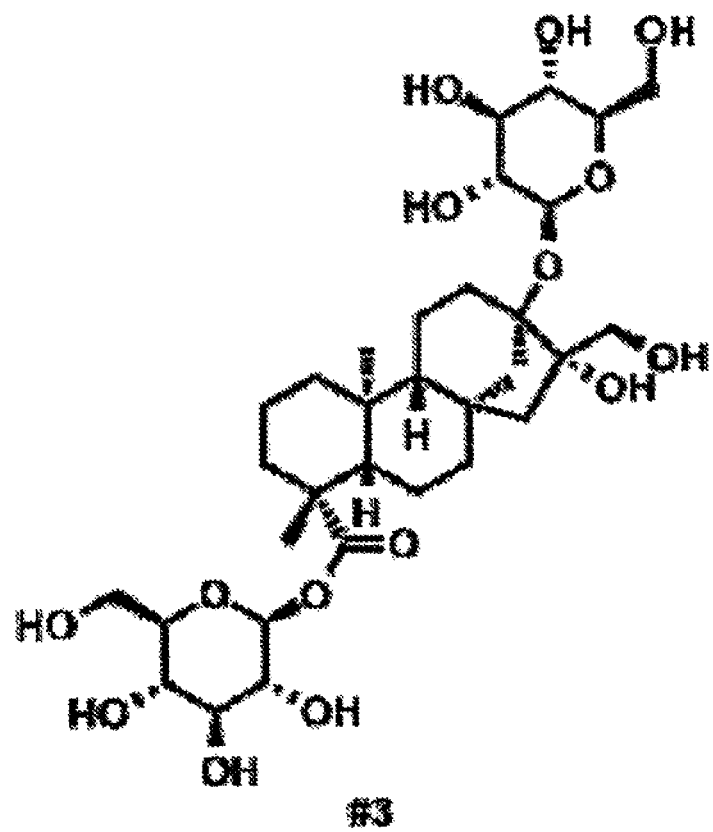
FIG. 6 shows the structure of RSG3 (Related Steviol Glycoside 3).
Figure 7:
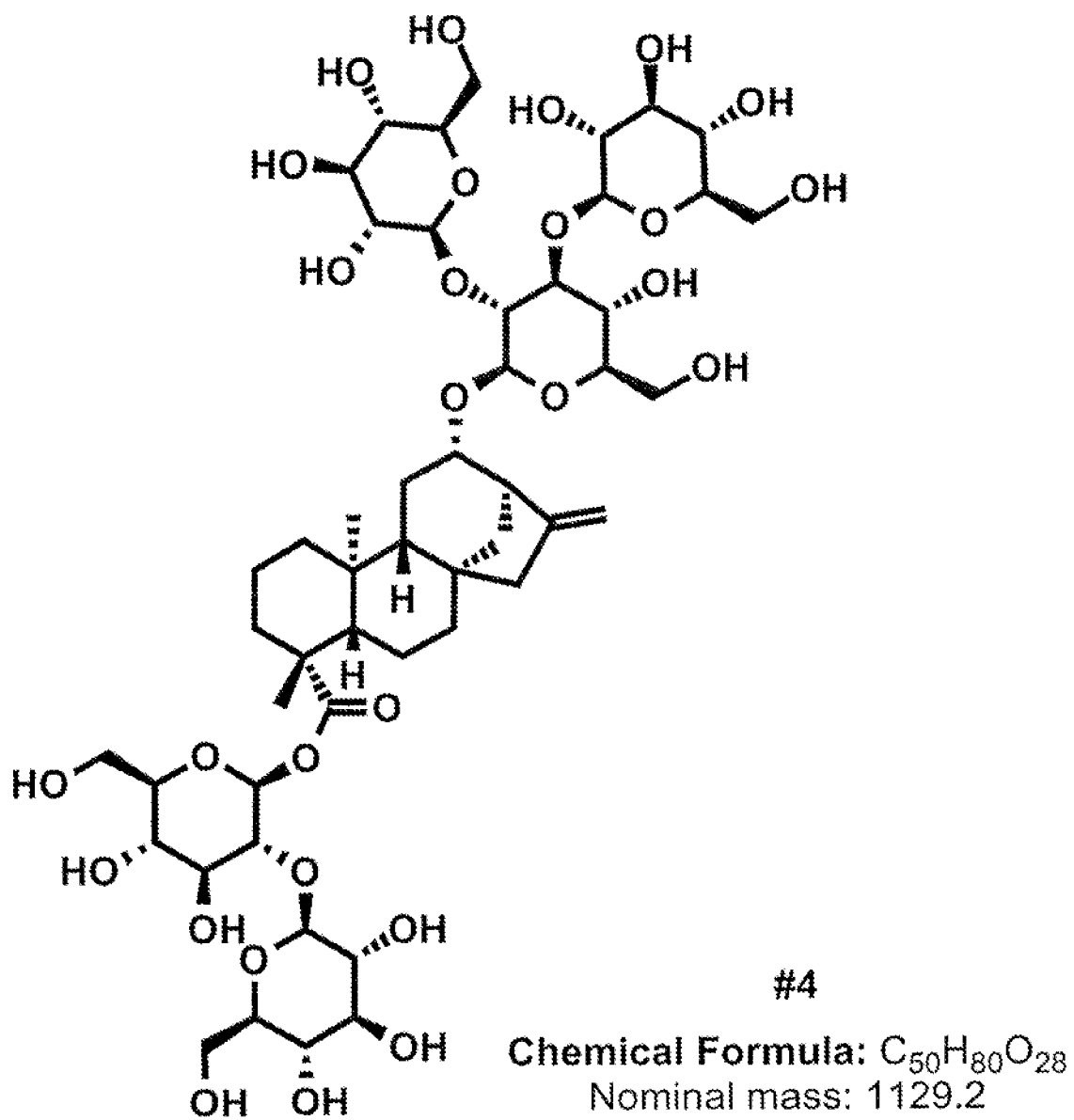
FIG. 7 shows the structure of RSG4 (Related Steviol Glycoside 4).
Figure 8:
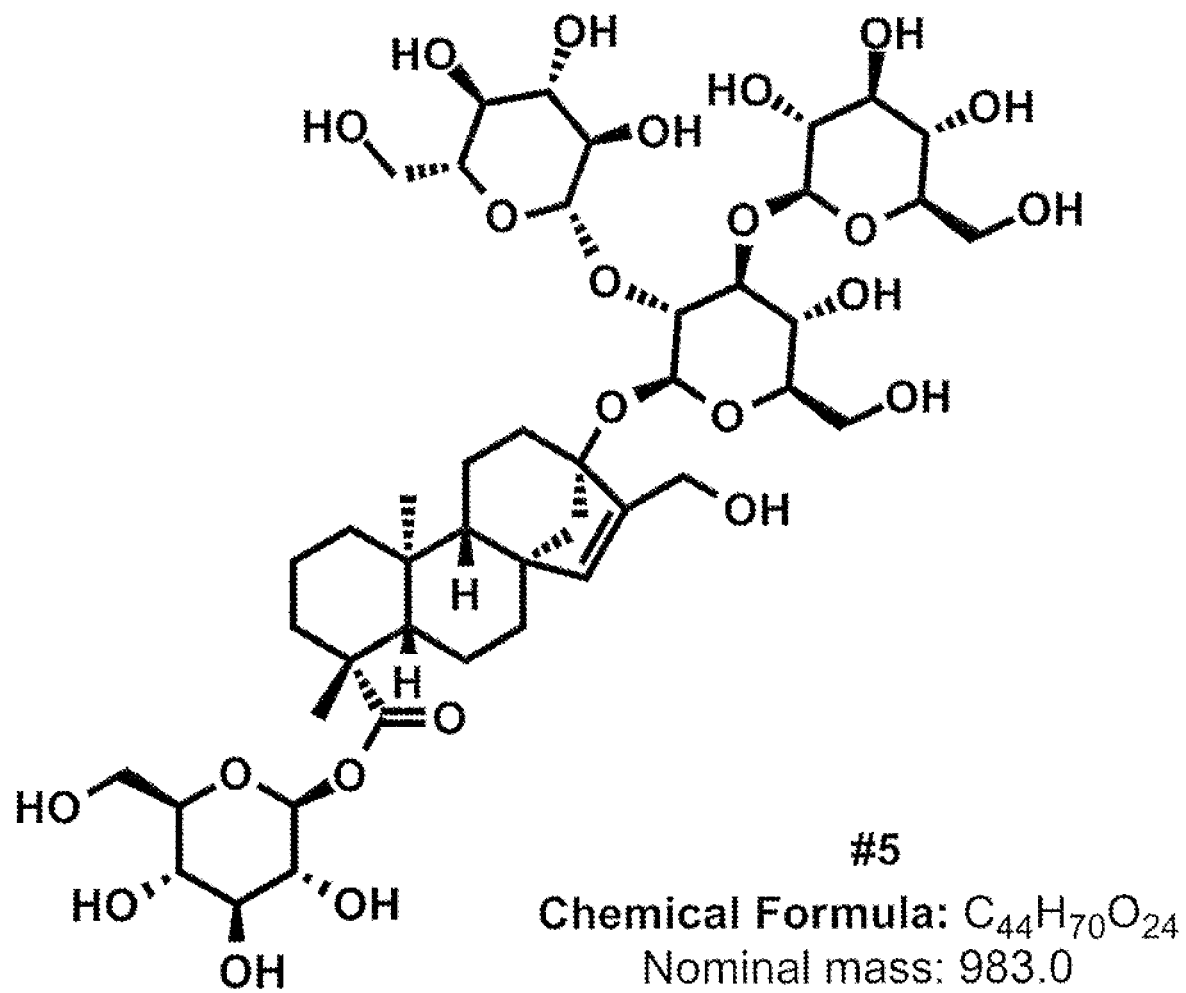
FIG. 8 shows the structure of RSG5 (Related Steviol Glycoside 5).
Figure 9:
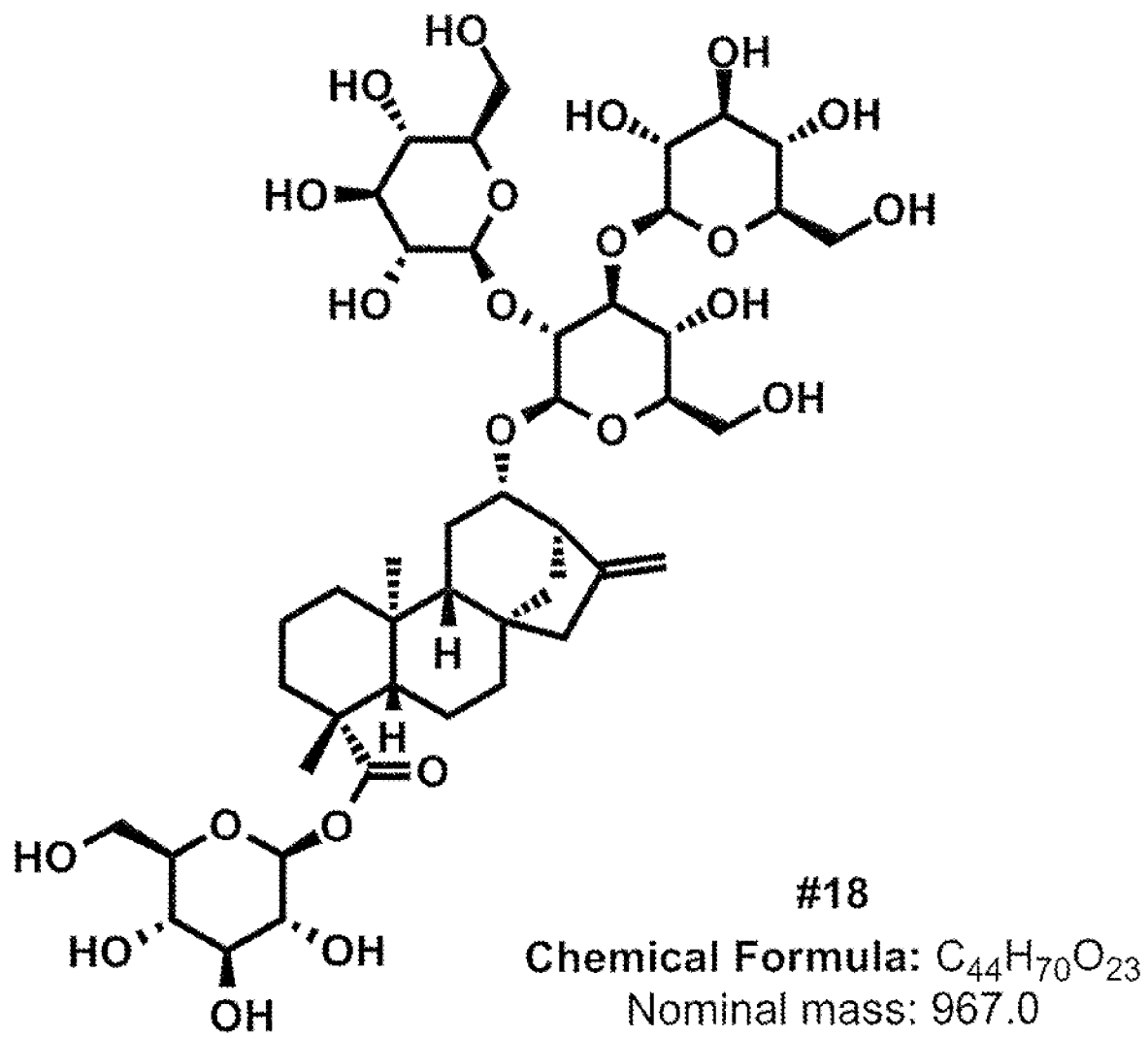
FIG. 9 shows the structure of RSG6 (Related Steviol Glycoside 6).
Figure 10:
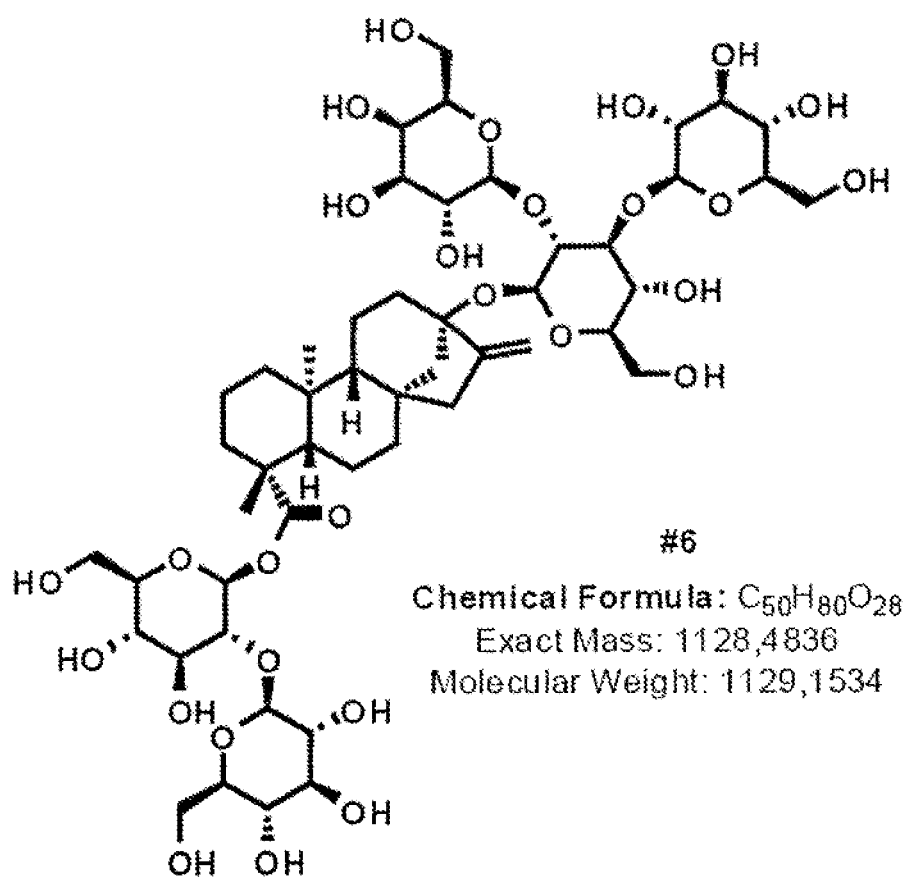
FIG. 10 shows the structure of Rebaudioside T.
Figure 11:
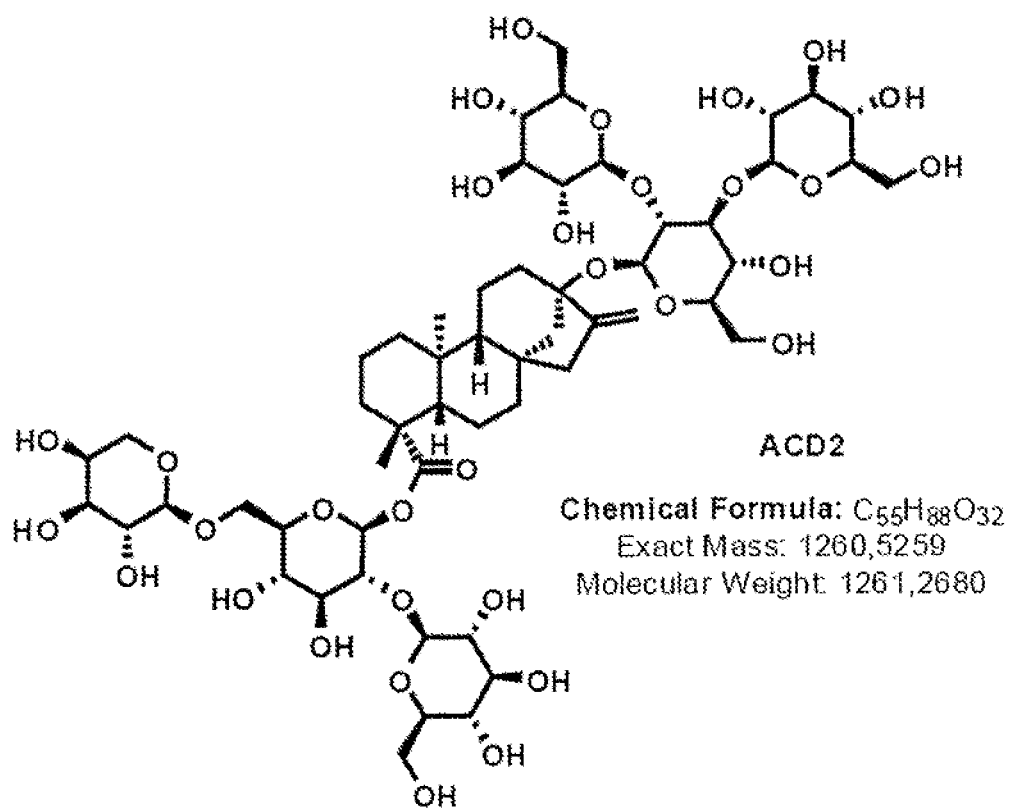
FIG. 11 shows the structure of Rebaudioside Y.
Figure 12:
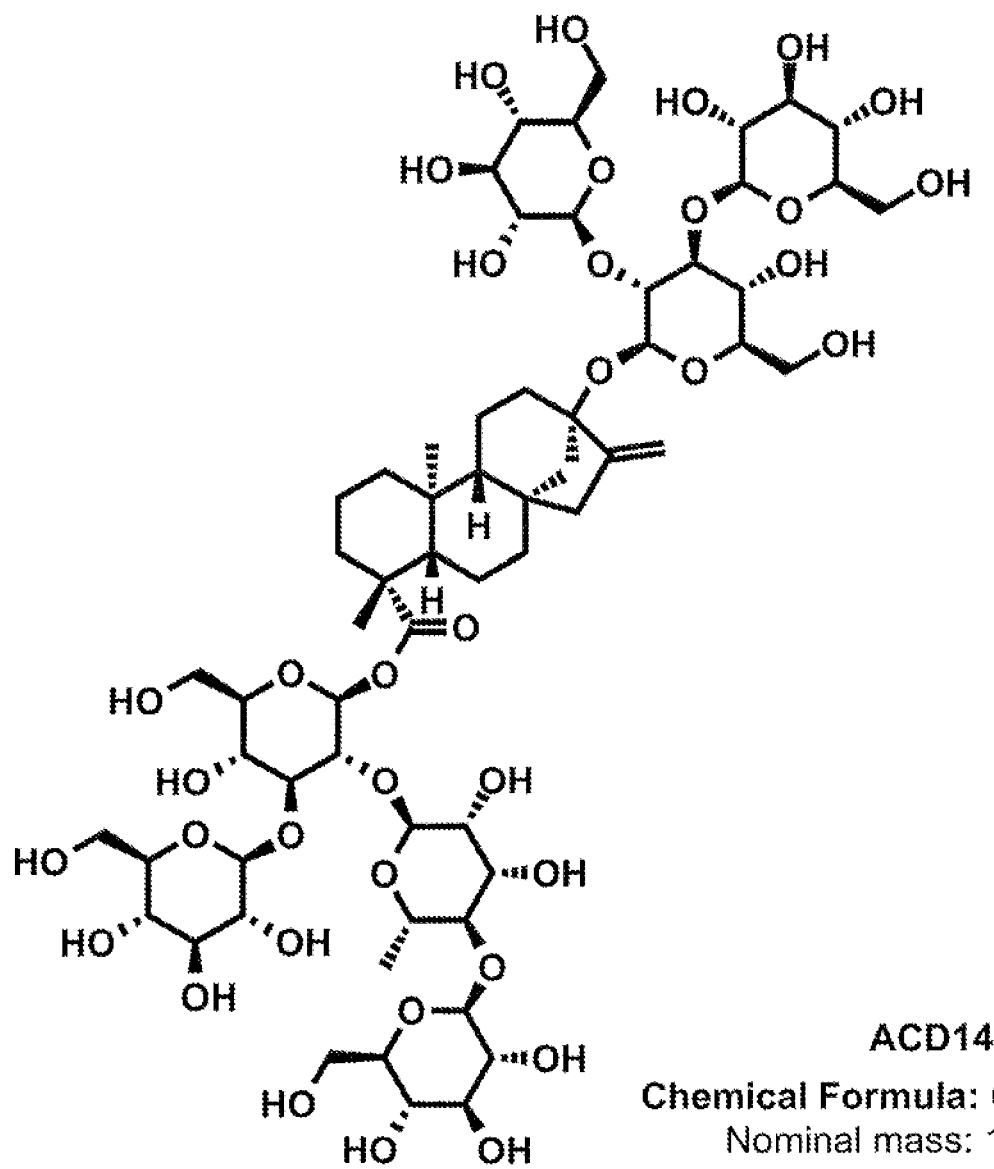
FIG. 12 shows the structure of Rebaudioside O2.
Figure 13:
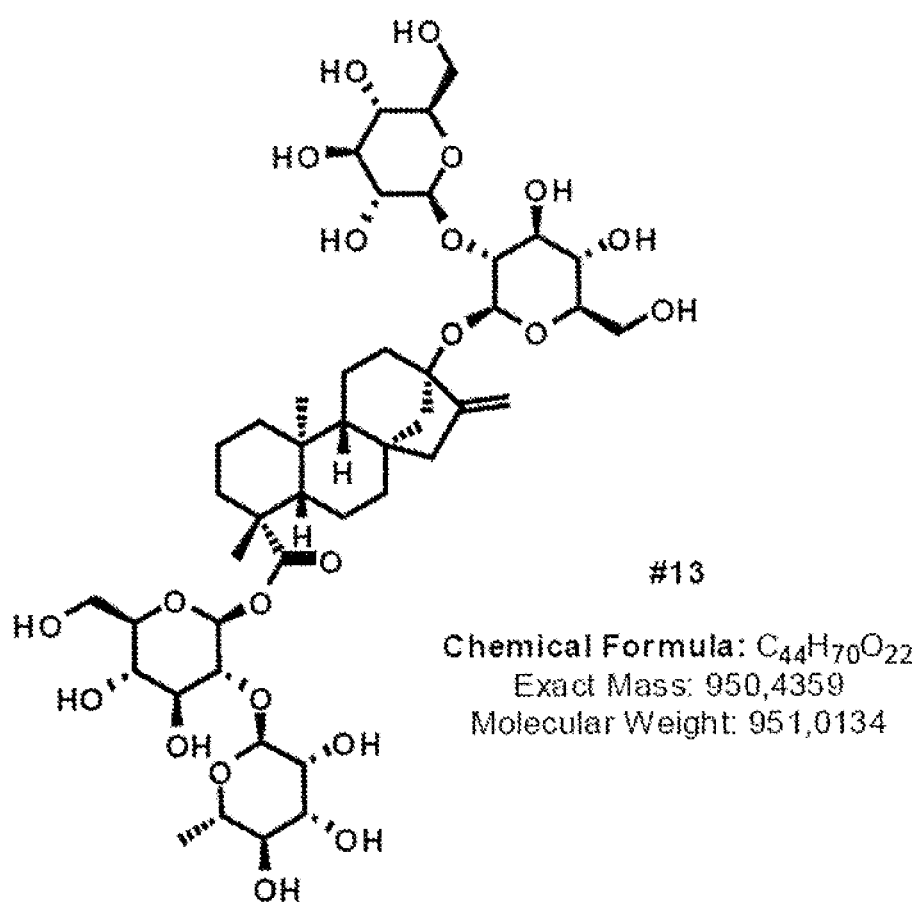
FIG. 13 shows the structure of Rebaudioside C2.
Figure 14:
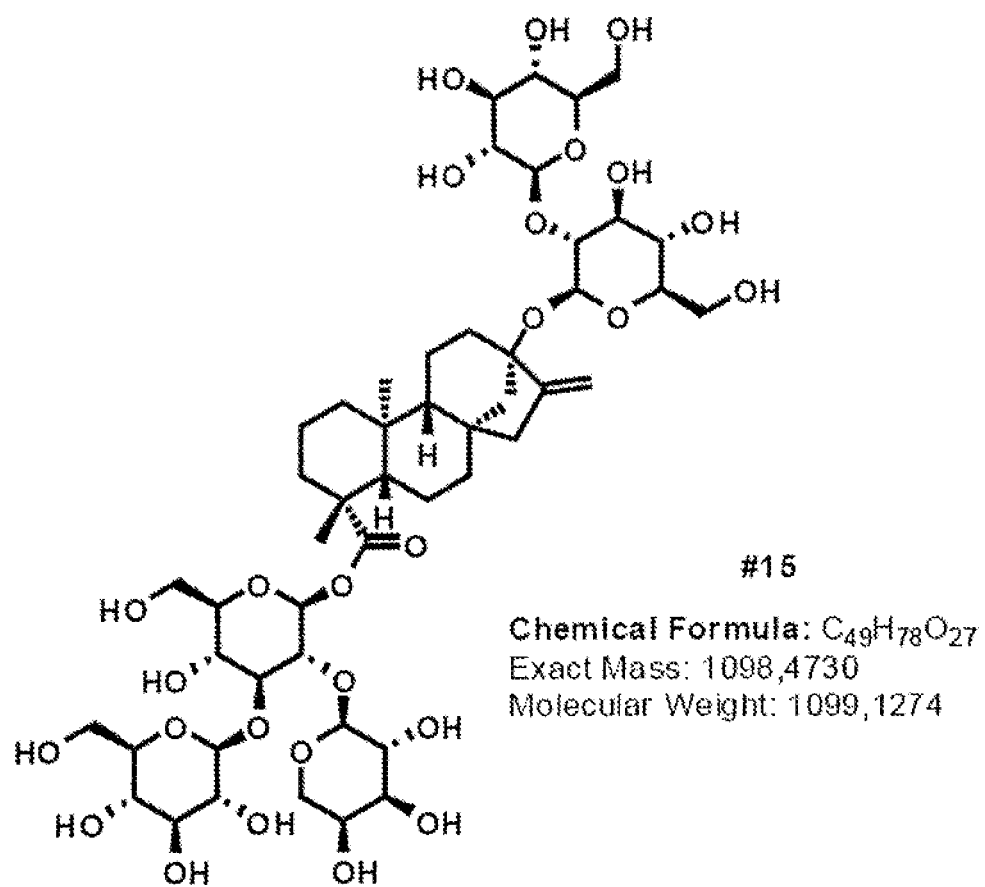
FIG. 14 shows the structure of Rebaudioside W.
Figure 15:
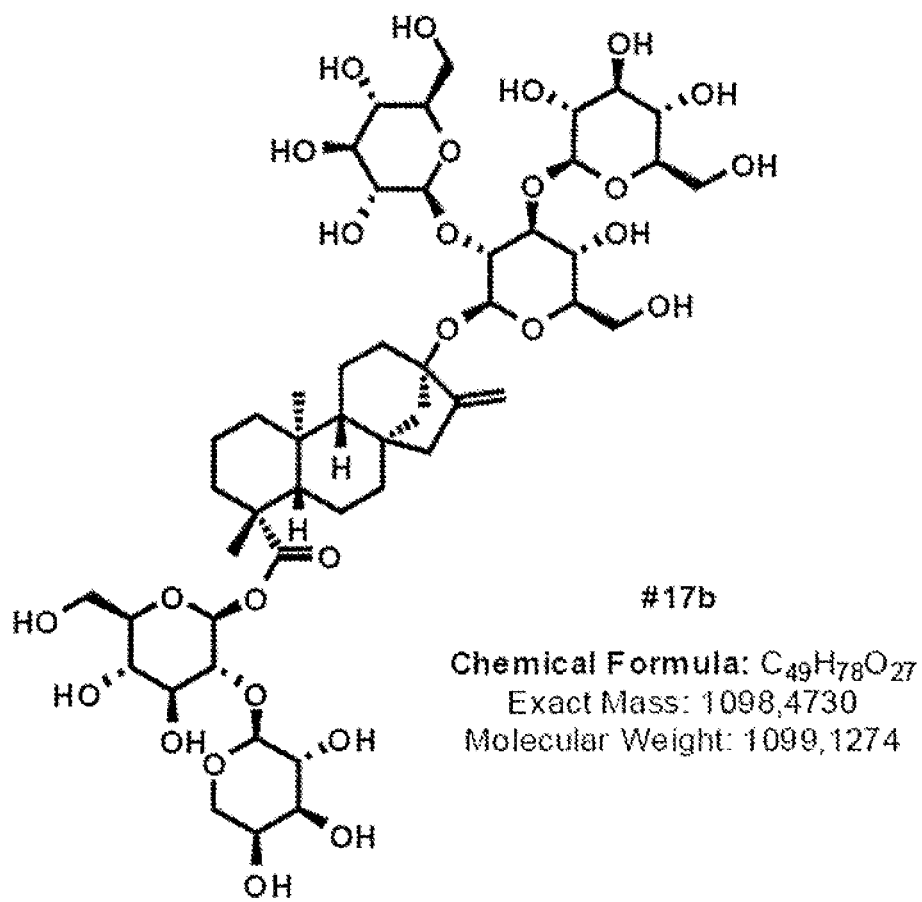
FIG. 15 shows the structure of Rebaudioside W2.
Figure 16:
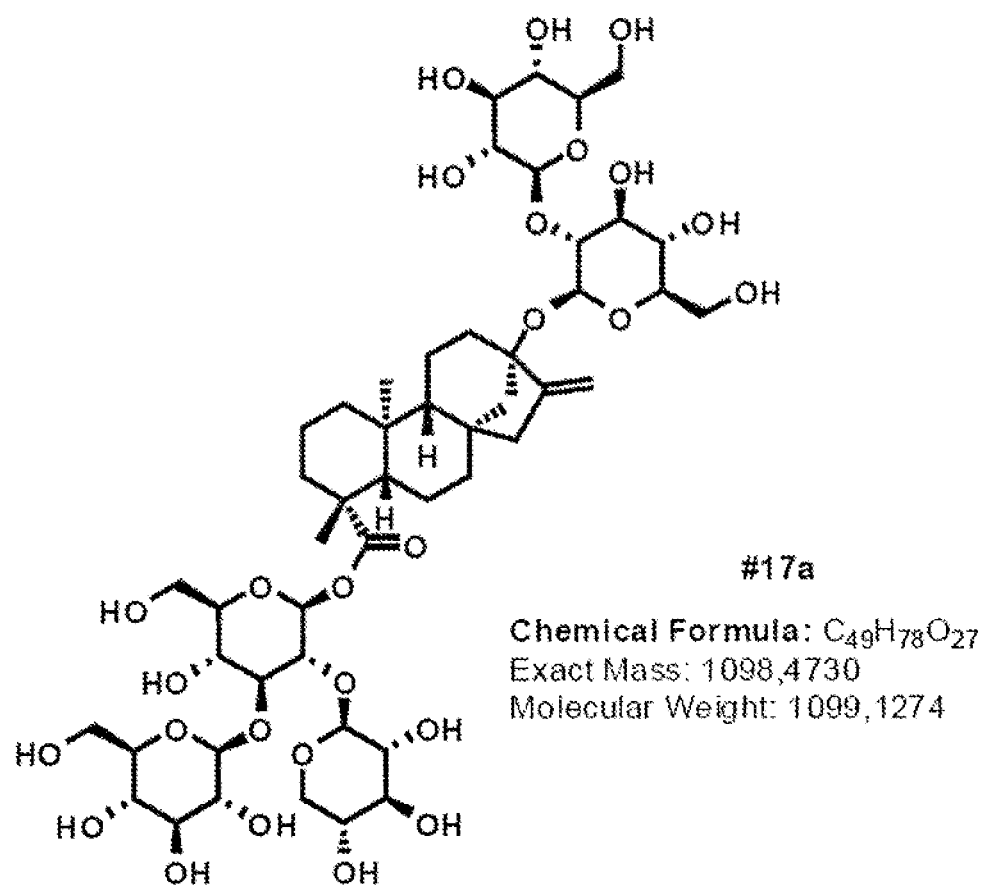
FIG. 16 shows the structure of Rebaudioside U2.

FIG. 1 shows the HPLC chart containing the major peaks identified in Table 7 by using analytical methodology as described above. The schematic steps to isolate different compounds in Table 7 are shown in FIG. 2 and FIG. 3.

A list of novel *stevia*-leaf-derived molecules isolated by using the method of Example 1 is shown in Table 8 and Table 9.

TABLE 8

Related Steviol Glycoside Components

| Related Steviol Glycoside Components (Peak ID) | Molecular Weight | Trivial Formula | Formula | Retention time (min) |
|---|---|---|---|---|
| RSG1 (#1) | 458 | NA | C21H30O11 | 6.97 |
| RSG2 (#2) | 982 | NA | C44H70O24 | 6.99 |
| RSG3 (#3) | 676 | NA | C32H52O15 | 7.32 |
| RSG4 (#4) | 1128 | NA | C50H80O28 | 7.64 |
| RSG5 (#5) | 982 | NA | C44H70O24 | 8.56 |

TABLE 9

Novel Steviol Glycoside Components

| Steviol Glycoside (Peak ID) | Molecular Weight | Trivial Formula | Formula | Retention Time (min) |
|---|---|---|---|---|
| Rebaudioside T (#6) | 1128 | SvGal1G4 | C50H80O28 | 8.95 |
| Rebaudioside Y (#ACD 2) | 1260 | SvA1G5 | C55H88O32 | — |
| Rebaudioside O2 (#ACD 14) | 1436 | SvR1G6 | C52H100O37 | — |

TABLE 7

| Peak Identifier | Formula (based on structure) | Trivial Formula | KM7 tr (min) | Base Peak Mass | Fraction ID | MW |
|---|---|---|---|---|---|---|
| #1 | $C_{21}H_{30}O_{11}$ | | 6.97 | 517.3 | C-2314-B-07 | 458 |
| #2 | $C_{44}H_{70}O_{24}$ | | 6.99 | 981.4 | C-2293-E-02_NF2 | 982 |
| #3 | $C_{32}H_{52}O_{15}$ | | 7.32 | 735.4 | C-2283-C-07_NF2 | 676 |
| #4 | $C_{50}H_{80}O_{28}$ | | 7.64 | 1127.4 | C-2374-I-05 | 1128 |
| #5 | $C_{44}H_{70}O_{24}$ | | 8.56 | 981.4 | C-2314-B-12 | 982 |
| #6 | $C_{50}H_{80}O_{28}$ | SvGal1G4 | 8.95 | 1127.5 | C-2376-E-09 | 1128 |
| ACD1 | | | | 965.1 | C-2387-K | 966 |
| ACD2 | $C_{55}H_{88}O_{32}$ | SvA1G5 | | 1259.5 | C-2376-E-12 | 1260 |
| ACD14 | $C_{62}H_{100}O_{37}$ | SvR1G6 | | | C-2376-E-15 | 1436 |
| #7 REB E | $C_{44}H_{70}O_{23}$ | SvG4 | 10.37 | 965.1 | C-2321-E-E09 | 966 |
| #8 REB O | $C_{52}H_{100}O_{37}$ | SvR1G6 | 11.45 | 1435.0 | C-2348-G-04 | 1436 |
| #9 REB D | $C_{50}H_{80}O_{28}$ | SvG5 | 12.16 | 1127.1 | C-2340-N-A01 | 1128 |
| #10 REB K | $C_{50}H_{80}O_{27}$ | SvR1G4 | 12.69 | 1111.1 | C-2293-E-07_NF2 | 1112 |
| #11 REB N | $C_{56}H_{90}O_{32}$ | SvR1G5 | 13.19 | 1273.1 | C-2321-I-04 | 1274 |
| #12 REB M | $C_{56}H_{90}O_{33}$ | SvG6 | 15.22 | 1289.5 | C-2340-N-12 | 1291 |
| #13 | $C_{44}H_{70}O_{22}$ | SvR1G3 | 15.79 | 949.2 | C-2353-K-03 | 950 |
| #14 REB J | $C_{50}H_{80}O_{27}$ | SvR1G4 | 16.46 | 1111.1 | C-2340-N-03 | 1112 |
| #15 | $C_{49}H_{78}O_{27}$ | SvA1G4 | 17.93 | 1097.1 | C-2353-K-05 | 1098 |
| #16 | | | 18.31 | 1289.4 | | |
| #17b | $C_{49}H_{78}O_{27}$ | SvA1G4 | | 1097.5 | C-2376-D-09 | 1098 |
| #17a | $C_{49}H_{78}O_{27}$ | SvX1G4 | 18.80 | 1097.5 | C-2376-B-02 | 1098 |
| #18 | $C_{44}H_{70}O_{23}$ | | 19.49 | 965.2 | C-2376-D-03 | 966 |
| #19 | $C_{49}H_{78}O_{27}$ | SvA1G4 | 20.26 | 1097.4 | C-2348-F-11 | 1098 |
| ACD6 | $C_{55}H_{88}O_{32}$ | SvX1G5 | 20.95 | 1259.6 | C-2374-D-10 | 1260 |
| #20 | $C_{49}H_{78}O_{27}$ | SvXG4 | 21.14 | 1097.4 | C-2283-F-11_NF2 | 1098 |
| #21 | $C_{50}H_{80}O_{27}$ | SvR1G4 | 23.31 | 1111.4 | C-2374-D-07 | 1112 |
| #22 | $C_{55}H_{88}O_{32}$ | SvX1G5 | 25.51 | 1259.6 | C-2283-F-14_NF2 | 1260 |
| #23 REB H | $C_{50}H_{80}O_{27}$ | SvR1G4 | 30.71 | 1111.5 | C-2321-F-08_NF2 | 1112 |
| #24 | | | 32.14 | 1111.5 | | |
| #25 REB I | | SvG5 | 37.49 | 1127.5 | | |
| #26 REB A | $C_{44}H_{70}O_{23}$ | SvG4 | 40.32 | 965.1 | | 966 |
| #27 Stevioside | | SvG3 | 40.53 | 641.3 | | |
| #28 REB C | $C_{44}H_{70}O_{22}$ | SvR1G3 | 50.17 | 949.5 | | 950 |
| #29 REB B | $C_{38}H_{60}O_{18}$ | SvG3 | 53.76 | 803.5 | C-2321-B-22 | 804 |

TABLE 9-continued

Novel Steviol Glycoside Components

| Steviol Glycoside (Peak ID) | Molecular Weight | Trivial Formula | Formula | Retention Time (min) |
|---|---|---|---|---|
| Rebaudioside C2 (#13) | 950 | SvR1G3 | C44H70O22 | 15.79 |
| Rebaudioside W (#15) | 1098 | SvA1G4 | C49H78O27 | 17.93 |
| Rebaudioside W2 (#17b) | 1098 | SvA1G4 | C49H78O27 | NA |
| Rebaudioside U2 (#17a) | 1098 | SvX1G4 | C49H78O27 | 18.8 |
| Rebaudioside W3 (#19) | 1098 | SvA1G4 | C49H78O27 | 20.26 |
| Rebaudioside V (#ACD6) | 1260 | SvX1G5 | C55H88O32 | 20.95 |
| Rebaudioside U (#20) | 1098 | SvX1G4 | C49H78O27 | 21.14 |
| Rebaudioside K2 (#21) | 1112 | SvR1G4 | C50H80O27 | 23.31 |
| Rebaudioside V2 (#22) | 1260 | SvX1G5 | C55H88O32 | 25.51 |

Example 2: Identification and Characterization of a Novel Compound

This Example outlines the isolation, identification and characterization of Rebaudioside W3 (#19) as an example. Similar analysis was carried out for all novel steviol glycoside molecules.

Isolation 100 g *stevia* leaf extract A95 were recrystallized according to the method described in section 1.3 (Example 1) yielding 33.2 g of enriched minor compounds from mother liquor. The enriched minor compounds were fractionated using normal phase chromatography as described in section 1.5 using gradient A (see Table 4). Fractions 49-60 yielded 1.32 g of enriched minor compounds which were further fractionated using reversed phase HPLC according to section 1.4 using gradient L.

RP (Reversed Phase)—HPLC & LCMS

Figure 17A:
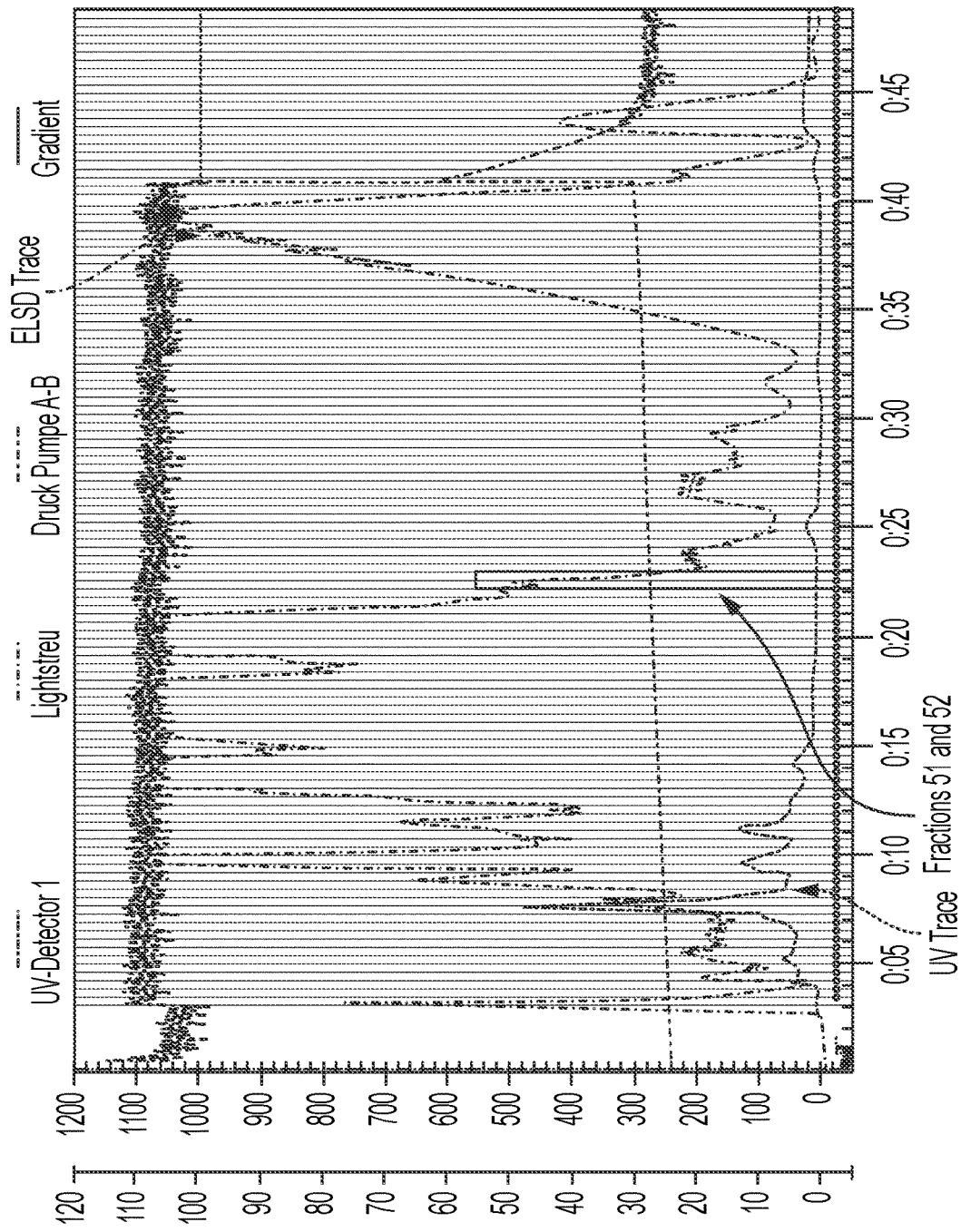
FIG. 17A shows an RP-HPLC analysis of selected fractions of stevia leaf extract.
Figure 17B:
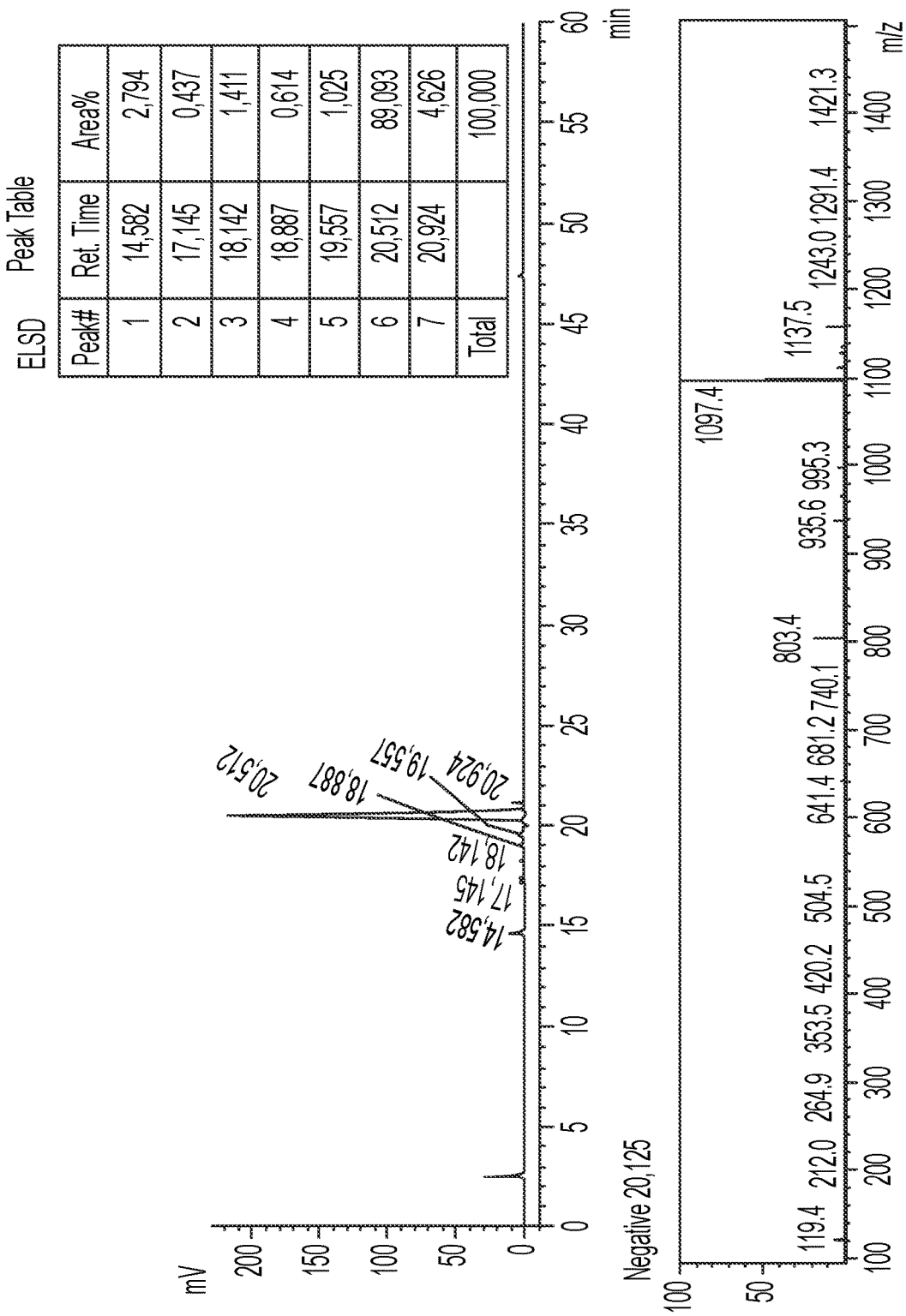
FIG. 17B shows ELSD and MS analysis of selected fractions of stevia leaf extract.

Fractions 51+52 are marked (FIG. 17A) by a red rectangle, ELSD trace (blue) and UV trace (orange) yielded 37.5 mg of #19. Fractions 66+67 (FIG. 17B) with preparative RP-HPLC chromatogram yielded 3.85 g of enriched minor compounds, Fractions 66+67 were analyzed by LCMS according to section 3.2 (see FIG. 17B). 37.5 mg of compound #19 were obtained with 89% purity (ELSD).

NMR

Figure 17C:
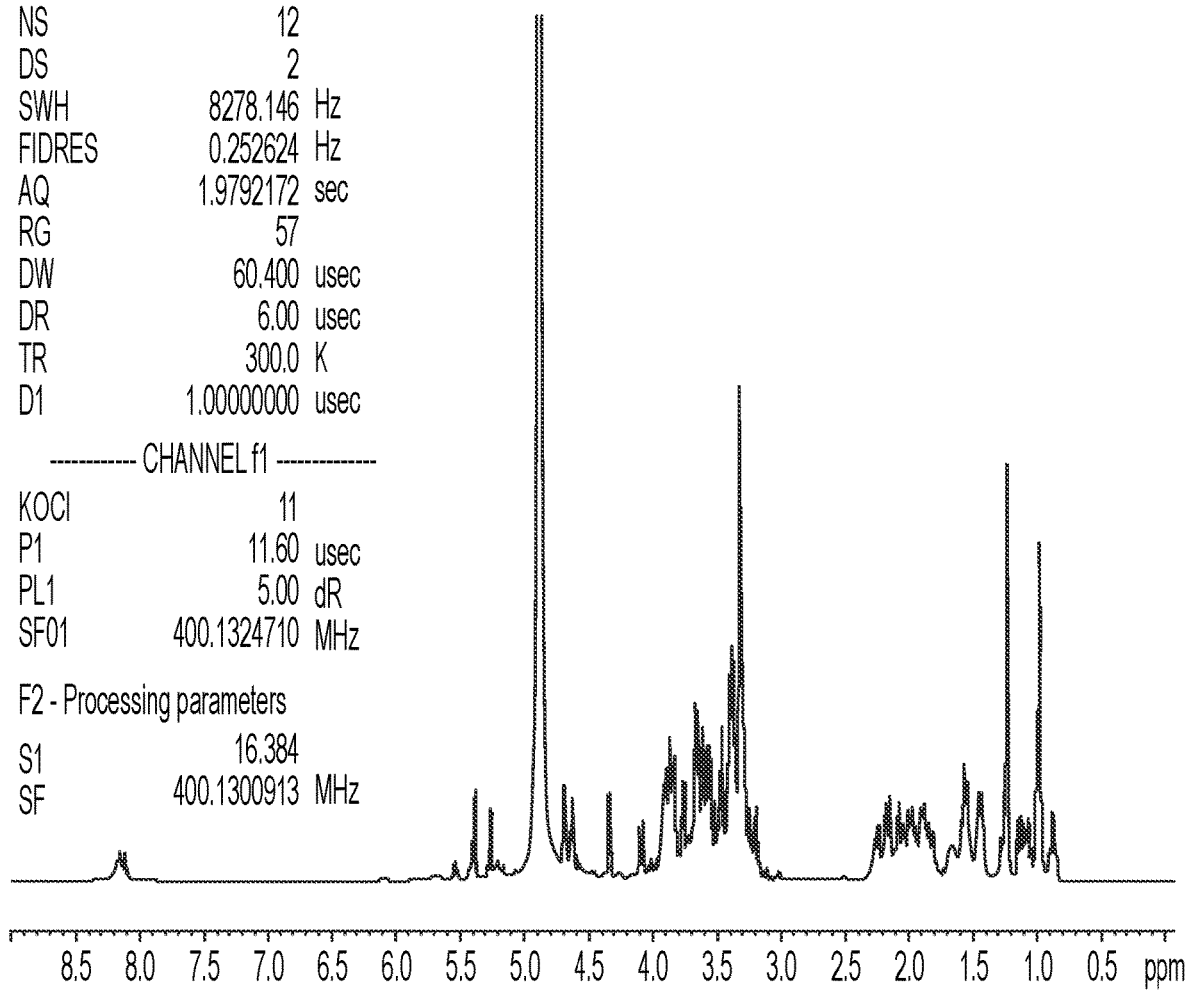
FIG. 17C shows $^1$H-NMR analysis of selected fractions of stevia leaf extract.
Figure 17D:
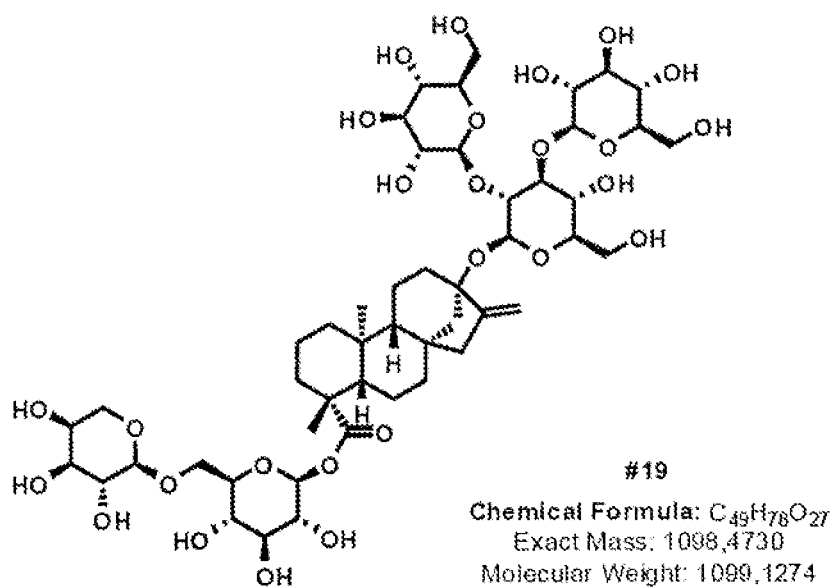
FIG. 17D shows the structure of Rebaudioside W3.
Figure 18:
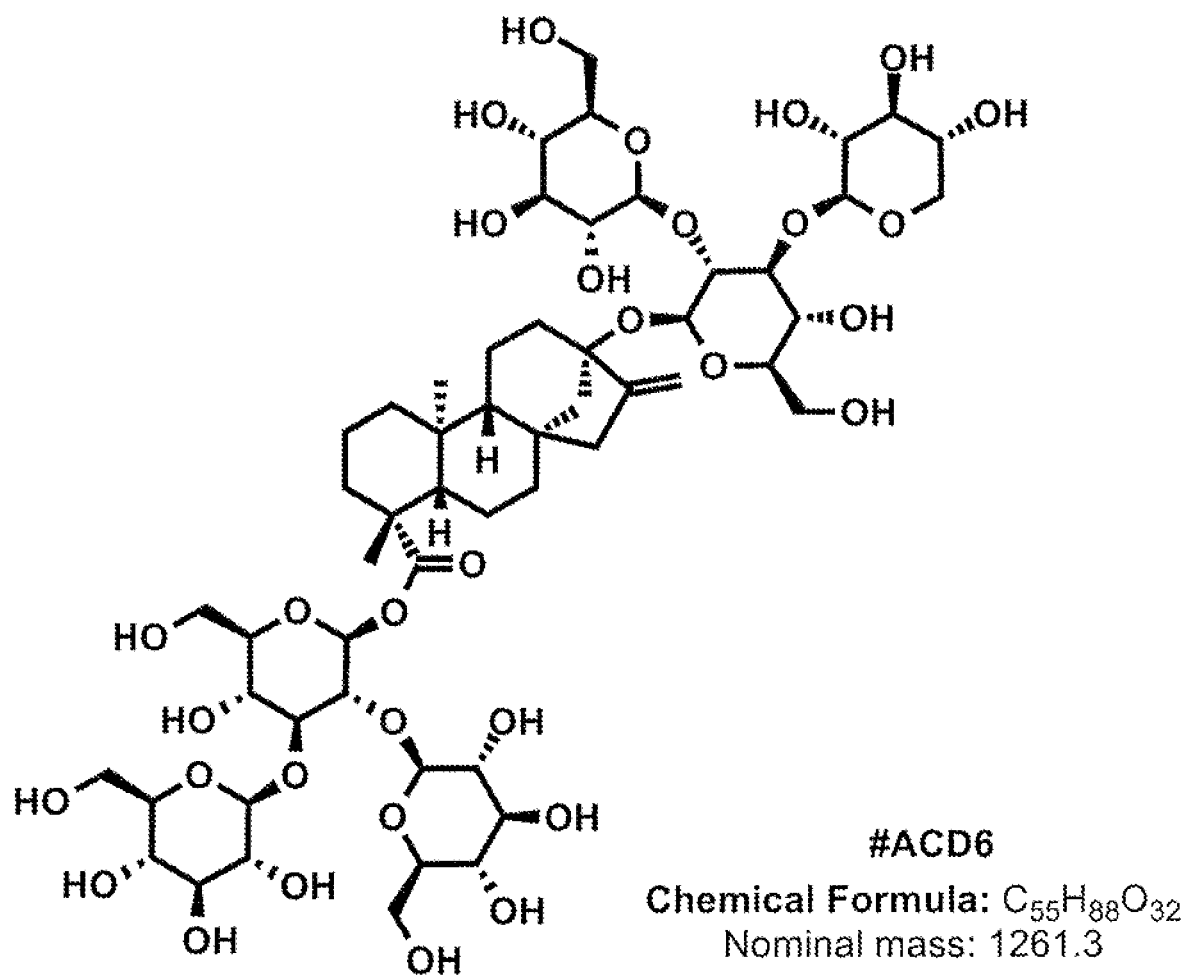
FIG. 18 shows the structure of Rebaudioside V.
Figure 19:
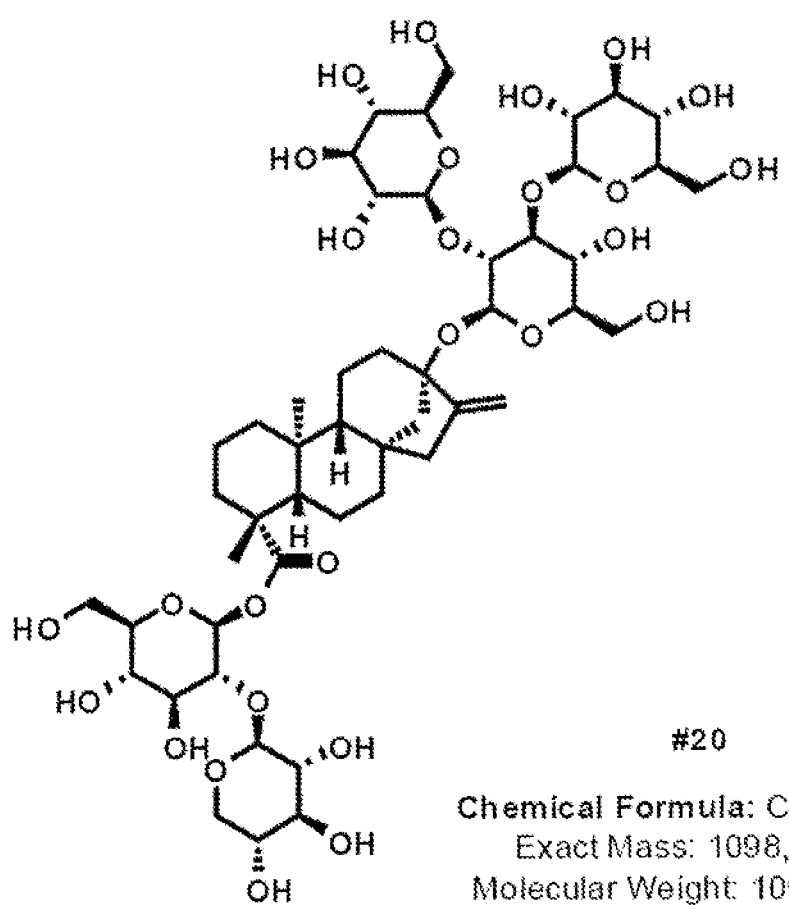
FIG. 19 shows the structure of Rebaudioside U.
Figure 20:
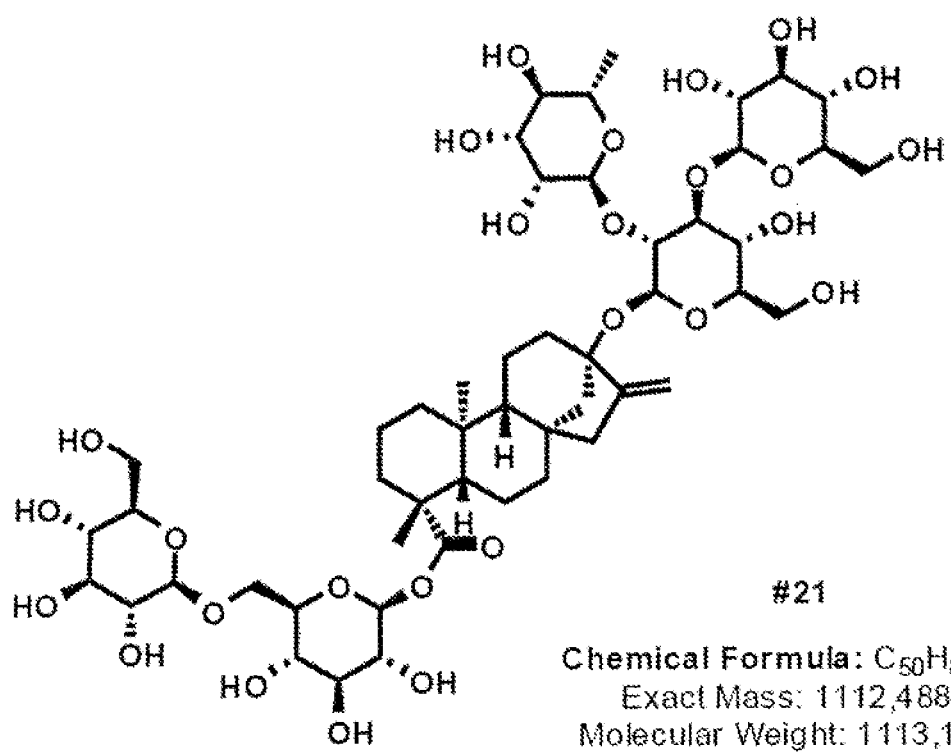
FIG. 20 shows the structure of Rebaudioside K2.
Figure 21:
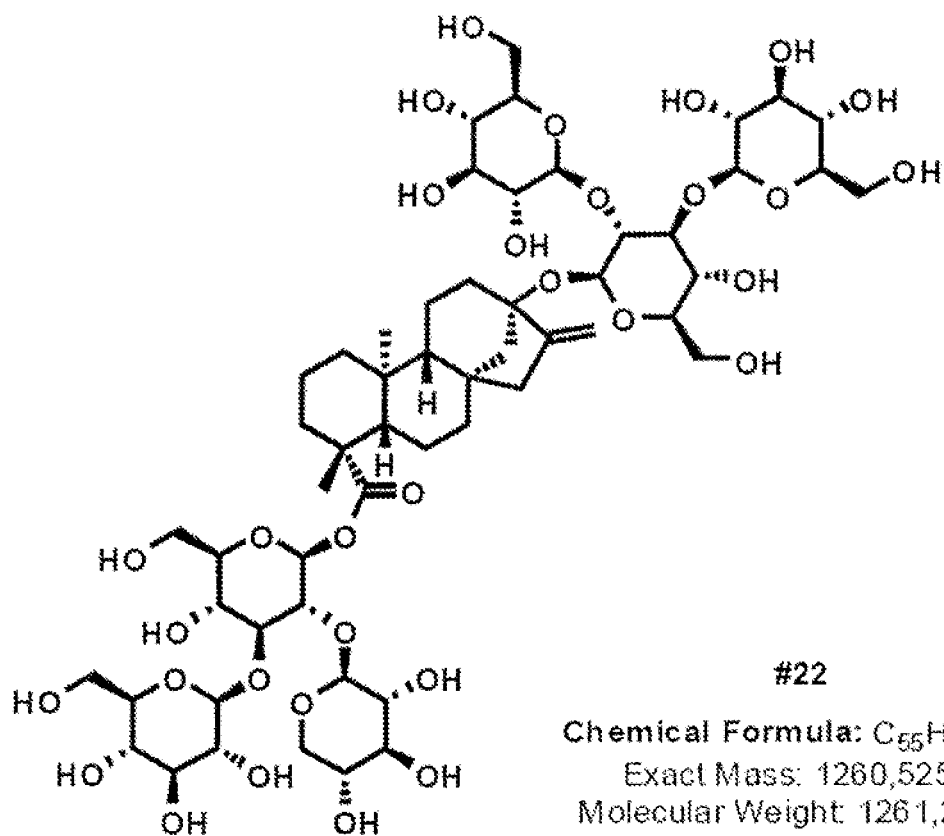
FIG. 21 shows the structure of Rebaudioside V2.

The structure of compound #19 was determined by NMR on a 500 MHz Bruker-NMR in $d_4$-Methanol ($\delta_C$=48.5 ppm; $\delta_H$=3.3 ppm). The data are shown in Table 10 and the NMR analysis is shown in FIG. 17C. The structure of compound #19 is shown in FIG. 17D.

TABLE 10

Assignment of the $^1$H-and $^{13}$C-NMR-Signals (based on HH-COSY, HSQC, HMBC and HSQC-TOCSY experiments)

| Position | $\delta_C$ [ppm] | $\delta_H$ [ppm] | J [Hz]/(INT) | HMBC (H -> C) |
|---|---|---|---|---|
| | | Aglycon moiety | | |
| 1 | 40.6 t | 0.87 m | | |
| | | 1.90 m | | |
| 2 | 19.1 t | 1.46 m | | |
| | | 1.96 m | | |
| 3 | 37.4 t | 1.56 m | | |
| | | 1.98 | | |
| 4 | 43.5 s | — | | |
| 5 | 57.5 d | 1.15 m | | |
| 6 | 21.9 t | 1.88 m | | |
| | | 2.03 | | |
| 7 | 41.7 t | 1.48 m | | |
| | | 1.60 m | | |
| 8 | 54.0 s | — | | |
| 9 | 54.2 d | 1.00 m | | |
| 10 | 39.0 s | — | | |
| 11 | 19.6 t | 1.67 m | | |
| | | 1.80 m | | |
| 12 | 38.0 t | 1.08 m | | |
| | | 2.17 m | | |
| 13 | 87.6 s | — | | |
| 14 | 44.2 t | 1.59 d | 11.6 | |
| | | 2.25 d | 11.6 | |
| 15 | 47.5 t | 2.07 d | 15.9 | 7, 8, 9, 14 |
| | | 2.16 d | 15.9 | |
| 16 | 152.5 s | — | | |
| 17 | 104.7 t | 4.90 br s | | 13, 15, 16 |
| | | 5.26 br s | | |
| 18 | 27.7 q | 1.24 s | (3H) | 3, 4, 5, 19 |
| 19 | 177.3 s | — | | |
| 20 | 15.4 d | 0.99 s | (3H) | 1, 5, 9, 10 |
| | | Sugar moiety | | |
| | | β-D-Glucopyranoside | | |
| $1^i$ | 96.5 d | 4.64 d | 8.4 | 13 |
| $2^i$ | 79.0 d | 3.67 t | 8.4 | |
| $3^i$ | 86.7 d | 3.78 t | 8.4 | |
| $4^i$ | 69.6 d | 3.38 t | 8.4 | |
| $5^i$ | 77.5 d | 3.41 m | | |
| $6^i$ | 61.7 t | 3.68 m | | |
| | | 3.93 m | | |
| | | β-D-Glucopyranoside | | |
| $1^{ii}$ | 103.0 d | 4.87 d | 8.4 | $2^i$ |
| $2^{ii}$ | 74.8 d | 3.23 t | 8.4 | |
| $3^{ii}$ | 77.1 d | 3.29 t | 8.4 | |
| $4^{ii}$ | 71.2 d | 3.19 t | 8.4 | |
| $5^{ii}$ | 77.1 d | 3.26 m | | |
| $6^{ii}$ | 61.8 t | 3.66 m | | |
| | | 3.89 m | | |
| | | β-D-Glucopyranoside | | |
| $1^{iii}$ | 103.4 d | 4.70 d | 8.4 | $3^i$ |
| $2^{iii}$ | 74.5 d | 3.30 t | 8.4 | |
| $3^{iii}$ | 77.3 d | 3.33 t | 8.4 | |
| $4^{iii}$ | 70.2 d | 3.28 t | 8.4 | |
| $5^{iii}$ | 76.7 d | 3.35 m | | |
| $6^{iii}$ | 61.3 t | 3.67 m | | |
| | | 3.88 m | | |
| | | β-D-Glucopyranoside | | |
| $1^{iv}$ | 94.5 d | 5.40 d | 8.4 | 19 |
| $2^{iv}$ | 73.2 d | 3.37 t | 8.4 | |
| $3^{iv}$ | 77.5 d | 3.47 t | 8.4 | |
| $4^{iv}$ | 69.7 d | 3.45 t | 8.4 | |
| $5^{iv}$ | 76.6 d | 3.58 m | | |
| $6^{iv}$ | 67.9 t | 3.86 m | | |
| | | 4.09 m | | |
| | | β-D-Arabinopyranoside | | |
| $1^v$ | 103.7 d | 4.33 d | 8.4 | $6^{iv}$ |
| $2^v$ | 71.5 d | 3.60 t | | |
| $3^v$ | 73.0 d | 3.58 t | | |
| $4^v$ | 68.5 d | 3.83 br s | | |
| $5^v$ | 65.5 d | 3.53 m | | |
| | | 3.89 m | | |

Each of these minor molecules identified above, preferably at purity levels ranging from 80-99%, including 90-95% purity, 99% purity, and 89% purity and higher, either as isolated or in combination with other *stevia*-derived molecules, are believed to have numerous desirable effects on the sweetness, taste and flavor profiles of products containing *stevia*-based ingredients. These molecules can be useful in imparting specific tastes or modifying flavors, or both, in food, beverage, nutraceutical, pharmaceutical, and other comestible or consumable products.

It is to be understood that the foregoing description and specific embodiments shown herein are merely illustrative of the best mode of the invention and the principles thereof, and that modifications and additions may be easily made by those skilled in the art without departing for the spirit and scope of the invention, which is therefore understood to be limited only by the scope of the appended claims.

The invention claimed is:

1. A *stevia*-derived composition having taste imparting properties, flavor modifying properties, or a combination thereof, at a purity level of greater than 80%, comprising one or more molecules selected from the group consisting of:

a.

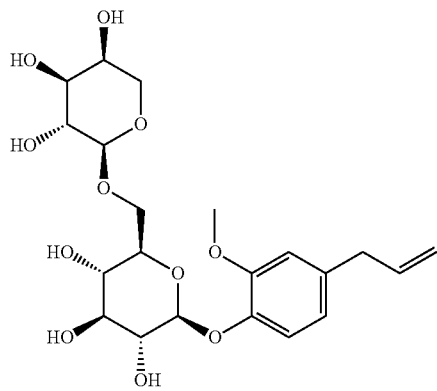

1

Chemical Formula: $C_{21}H_{30}O_{11}$
Exact Mass: 458.1788
Molecular Weight: 458.4563 c.

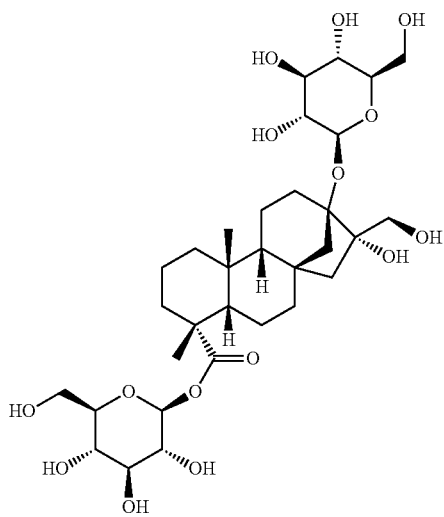

3

Chemical Formula: $C_{32}H_{52}O_{15}$
Exact Mass: 676.3306
Molecular Weight: 676.7463 d.

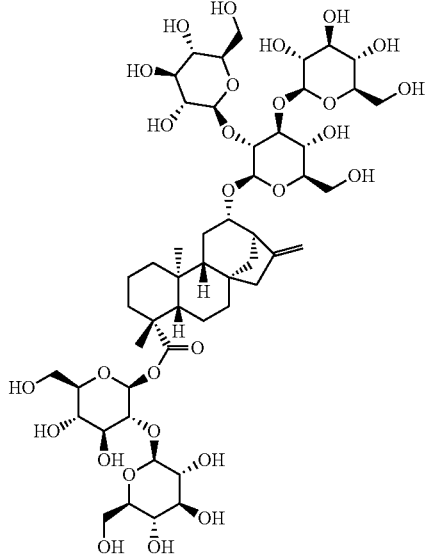

4

Chemical Formula: $C_{50}H_{80}O_{28}$
Nominal Mass: 1129.2 f.

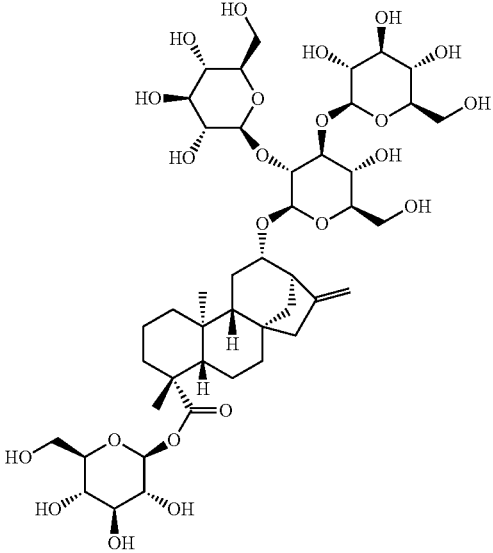

18

Chemical Formula: $C_{44}H_{70}O_{23}$
Nominal Mass: 967.0 h.
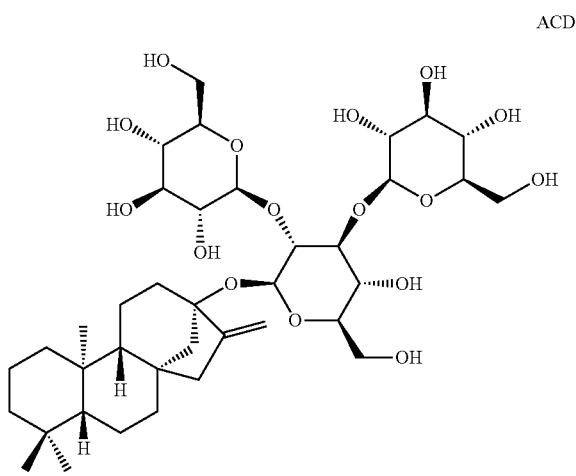
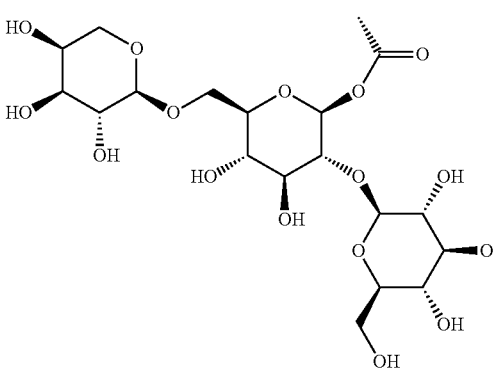
Chemical Formula: $C_{55}H_{88}O_{32}$
Exact Mass: 1260.5259
Molecular Weight: 1261.2680
j.
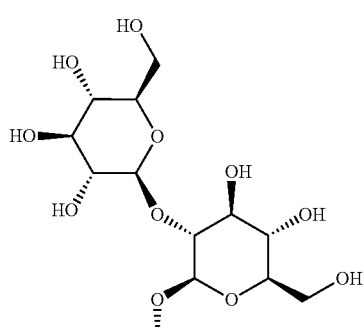
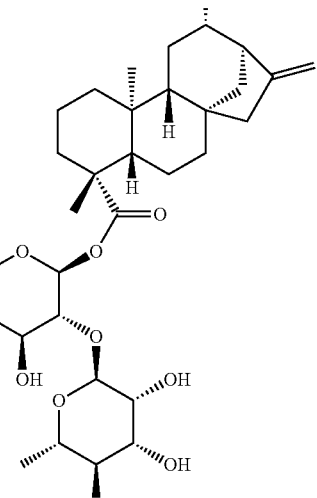
Chemical Formula: $C_{44}H_{70}O_{22}$
Exact Mass: 950.4359
Molecular Weight: 951.0134
k.
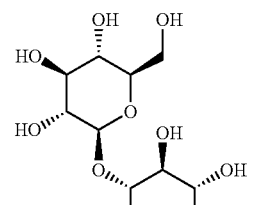
Chemical Formula: $C_{49}H_{78}O_{27}$
Exact Mass: 1098.4730
Molecular Weight: 1099.1274 l.
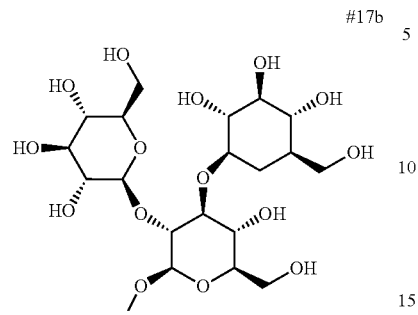
17b
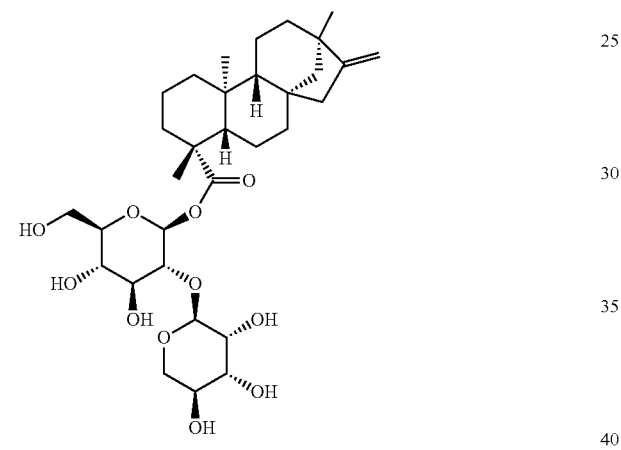
Chemical Formula: C$_{49}$H$_{78}$O$_{27}$
Exact Mass: 1098.4730
Molecular Weight: 1099.1274
m.
17a
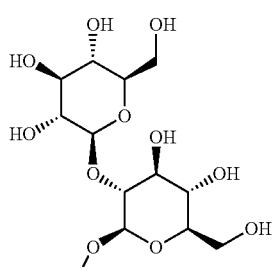
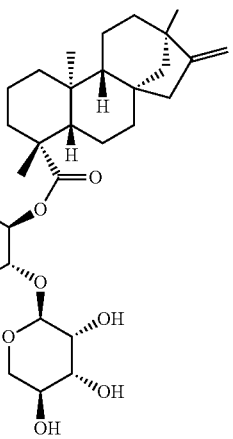
Chemical Formula: C$_{49}$H$_{78}$O$_{27}$
Exact Mass: 1098.4730
Molecular Weight: 1099.1274
n.
19
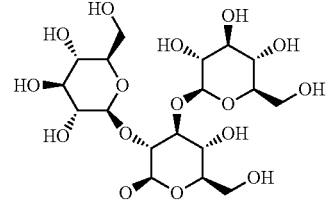
Chemical Formula: C$_{49}$H$_{78}$O$_{27}$
Exact Mass: 1098.4730
Molecular Weight: 1099.1274 o.
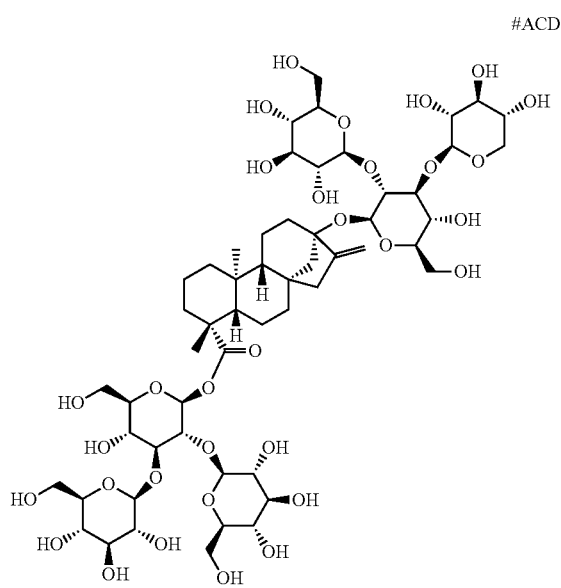
Chemical Formula: $C_{55}H_{88}O_{32}$
Nominal Mass: 1261.3
p.
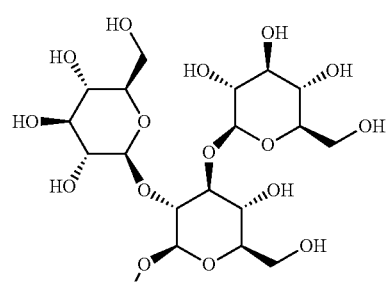
q.
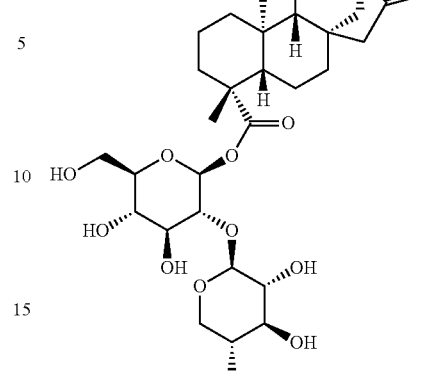
Chemical Formula: $C_{49}H_{78}O_{27}$
Exact Mass: 1098.4730
Molecular Weight: 1099.1274
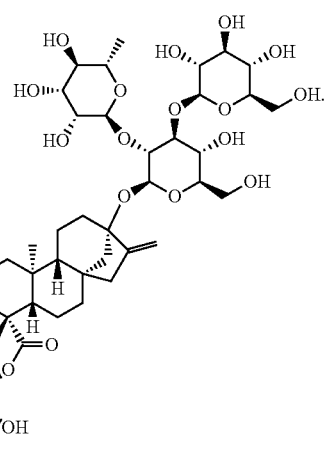
Chemical Formula: $C_{50}H_{80}O_{27}$
Exact Mass: 1112.4887
Molecular Weight: 1113.1540
2. A food, beverage, nutraceutical, pharmaceutical or other consumable product comprising the *stevia*-derived composition of claim 1.
* * * * *